(12) United States Patent  
Kuimelis et al.

(10) Patent No.: US 7,951,601 B2
(45) Date of Patent: May 31, 2011

(54) OXIDE LAYERS ON SILICON SUBSTRATES FOR EFFECTIVE CONFOCAL LASER MICROSCOPY

(75) Inventors: Robert G. Kuimelis, Palo Alto, CA (US); Zihui Chen, Mountain View, CA (US); Glenn H. McGall, Palo Alto, CA (US)

(73) Assignee: Affymetrix, Inc., Santa Clara, CA (US)

( * ) Notice: Subject to any disclaimer, the term of this patent is extended or adjusted under 35 U.S.C. 154(b) by 706 days.

(21) Appl. No.: 11/614,896

(22) Filed: Dec. 21, 2006

(65) Prior Publication Data

US 2007/0238185 A1    Oct. 11, 2007

Related U.S. Application Data

(60) Provisional application No. 60/754,534, filed on Dec. 28, 2005.

(51) Int. Cl.
  *G01N 33/00* (2006.01)
  *G01N 33/48* (2006.01)
(52) U.S. Cl. .............. 436/86; 436/91; 436/94; 436/93; 436/164; 436/172
(58) Field of Classification Search ............ 436/86; 438/723; 536/22.1; 524/155; 506/30
  See application file for complete search history.

(56) References Cited

U.S. PATENT DOCUMENTS 5,489,678 A * 2/1996 Fodor et al. .............. 506/30
5,527,681 A * 6/1996 Holmes ...................... 506/16
6,191,046 B1 * 2/2001 Singh et al. ................ 438/723
6,262,216 B1 * 7/2001 McGall ......................... 528/10
6,824,866 B1 * 11/2004 Glazer et al. ............... 428/317.9
2004/0087690 A1 * 5/2004 Lamanna et al. ........... 524/155

FOREIGN PATENT DOCUMENTS

EP    1 547 678    * 6/2005
EP    1547678       6/2005

OTHER PUBLICATIONS

Bras, M. et al. "Optimisation of a silicon/silicon dioxide substrate for a fluorescence DNA microarray," Biosens.Bioelectron., 20, Nov. 1, 2004, pp. 797-806.
Braun, Dieter,"Fluorescence interference-contrast microscopy of cell adhesion on oxidized silicon," Applied Physics, A65, 1997, pp. 341-348.
Braun, Dieter,"Fluorescence interferometry of neuraonal cell adhesion on microstructured silicon," The American Physical Society, 81, 1998, pp. 5241-5244.
Drexhage, Karl H.,"IV Interaction of Light with Monomolecular Dye Layers, In Progress in Optics", vol. 12, 1974, pp. 163-232.
Lambacher, Armin et al. "Fluorescence interference-contrast microscopy on oxidized silicon using a monomolecular dye layer," Applied Physics, A63, 1996, pp. 207-216.

* cited by examiner

*Primary Examiner* — Walter D Griffin
*Assistant Examiner* — Christine T Mui
(74) *Attorney, Agent, or Firm* — Steven M. Yee

(57) ABSTRACT

Methods of performing confocal laser microscopy on a polymer array disposed on a silicon wafer substrate, the method comprising the steps of providing a silicon wafer substrate having a top side and a bottom side, coating the top side of the silicon wafer with an oxide coating to provide an oxide coated wafer, covalently coupling a plurality of probes to the top side of the coated wafer to provide a fixed polymer array, hybridizing the fixed polymer array with a plurality of labeled ligands, and assaying for one or more hybridized ligands using confocal laser fluorescence microscopy to detect hybridization are provided.

10 Claims, 9 Drawing Sheets

OXIDE LAYERS ON SILICON SUBSTRATES FOR EFFECTIVE CONFOCAL LASER MICROSCOPY

FIELD OF THE INVENTION

The present invention relates to coated silicon substrates useful for array synthesis and subsequent fluorescence analysis of arrays.

BACKGROUND OF THE INVENTION

Methods for synthesizing a variety of different types of polymers are well known in the art. For example, the "Merrifield" method, described in Atherton et al., "Solid Phase Peptide Synthesis," IRL Press, 1989, has been used to synthesize peptides on a solid support. In the Merrifield method, an amino acid is covalently bonded to a support made of an insoluble polymer or other material. Another amino acid with an alpha protecting group is reacted with the covalently bonded amino acid to form a dipeptide. After washing, the protecting group is removed and a third amino acid with an alpha protecting group is added to the dipeptide. This process is continued until a peptide of a desired length and sequence is obtained.

Methods have also been developed for producing large arrays of polymer sequences on solid substrates. These large "array" of polymer sequences have wide ranging applications and are of substantial importance to the pharmaceutical, biotechnology and medical industries. For example, the arrays may be used in screening large numbers of molecules for biological activity, i.e., receptor binding capability. Alternatively, arrays of oligonucleotide probes can be used to identify mutations in known sequences, as well as in methods for de novo sequencing of target nucleic acids.

SUMMARY OF THE INVENTION

Embodiments of the present invention are based in part on the discovery that a variety of silicon substrates comprising an oxide layer are suitable for array synthesis and subsequent fluorescence analysis. A variety of silicon substrates were investigated and determined to be suitable to support silanation and non-photochemical methods of phosphoramidite-based probe synthesis, generating results that were comparable to results obtained using fused silica.

The present invention provides methods of performing confocal laser microscopy on a polymer array disposed on a silicon wafer substrate. In certain embodiments, a method of the invention includes providing a silicon wafer substrate having a top side and a bottom side, coating the top side of the silicon wafer with an oxide coating to provide an oxide coated wafer, covalently coupling a plurality of probes to the top side of the coated wafer to provide a fixed polymer array, hybridizing the fixed polymer array with a plurality of labeled ligands, and assaying for one or more hybridized ligands using confocal laser fluorescence microscopy to detect hybridization. Certain aspects of the invention include applying N(2-hydroxyethyl)-N,N bis(trimethoxysilylpropyl) amine to the oxide coating.

In other embodiments, the present invention provides a method of performing confocal laser microscopy on a polymer array disposed on a silicon wafer substrate including the steps of providing a silicon wafer substrate having a top side and a bottom side, coating the top side of the substrate with a transparent oxide layer to provide an oxide coated wafer, depositing a reactive functional group comprising a labile protecting group substantially uniformly across the transparent oxide layer, selectively removing one or more of the labile protecting groups from predefined regions of the wafer to provide exposed functional groups in said predefined regions, reacting the exposed functional groups with a monomer comprising a reactive functional group and a labile protecting group, repeating the steps of selectively removing and reacting to produce said polymer array, hybridizing the polymer array with a plurality of ligands, and assaying for one or more hybridized ligands using a confocal laser fluorescence microscopy to detect hybridization.

Certain aspects of the invention provide an oxide layer having a thickness of at least 3,500 angstroms or having a thickness of at least 35,000 angstroms. Other aspects of the invention provide that a labile protecting group is an acid labile protecting group such as a dimethoxytrityl group. Other aspects of the invention provide that an acid labile protecting group is removed by activating a photoacid generator with light of an appropriate wavelength to produce acid. A photoacid generator includes an ionic photoacid generator such as an onium salt such as bis-(4-t-butyl phenyl)iodonium $PF_6^-$, or a non-ionic photoacid generator such as 2,6-dinitrobenzyl tosylate.

Certain aspects of the invention provide that a labile protective group is a photolabile protecting group. Labile protecting groups include MeNPOC. In accordance with an aspect of the present invention, more efficient photolabile protecting groups can also be used. It has been discovered in accordance with the present invention that to achieve suitable primer purity and quantity, a highly-efficient photogroup (>90% average stepwise coupling efficiency) is preferred, as NPPOC or MBPMOC:

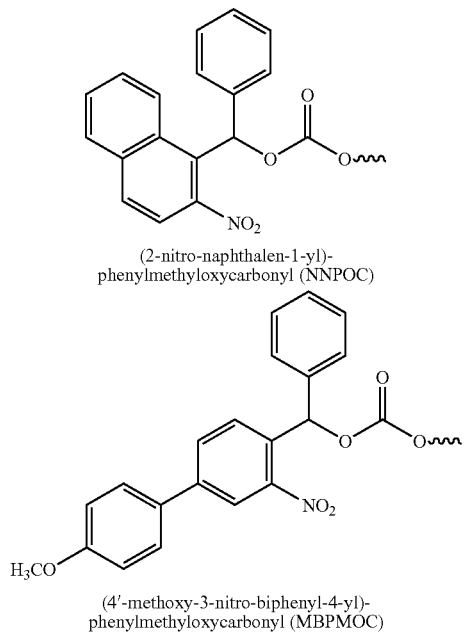

(2-nitro-naphthalen-1-yl)-phenylmethyloxycarbonyl (NNPOC)

(4'-methoxy-3-nitro-biphenyl-4-yl)-phenylmethyloxycarbonyl (MBPMOC)

Both NNPOC and MBPMOC give greater than 90% stepwise coupling. Other aspects of the invention provide that a monomer is a nucleotide, an nucleic acid, an amino acid or a peptide.

BRIEF DESCRIPTION OF THE DRAWINGS

The foregoing and other features and advantages of the present invention will be more fully understood from the following detailed description of illustrative embodiments taken in conjunction with the accompanying drawings in which.

DETAILED DESCRIPTION OF THE INVENTION

Figure 1:
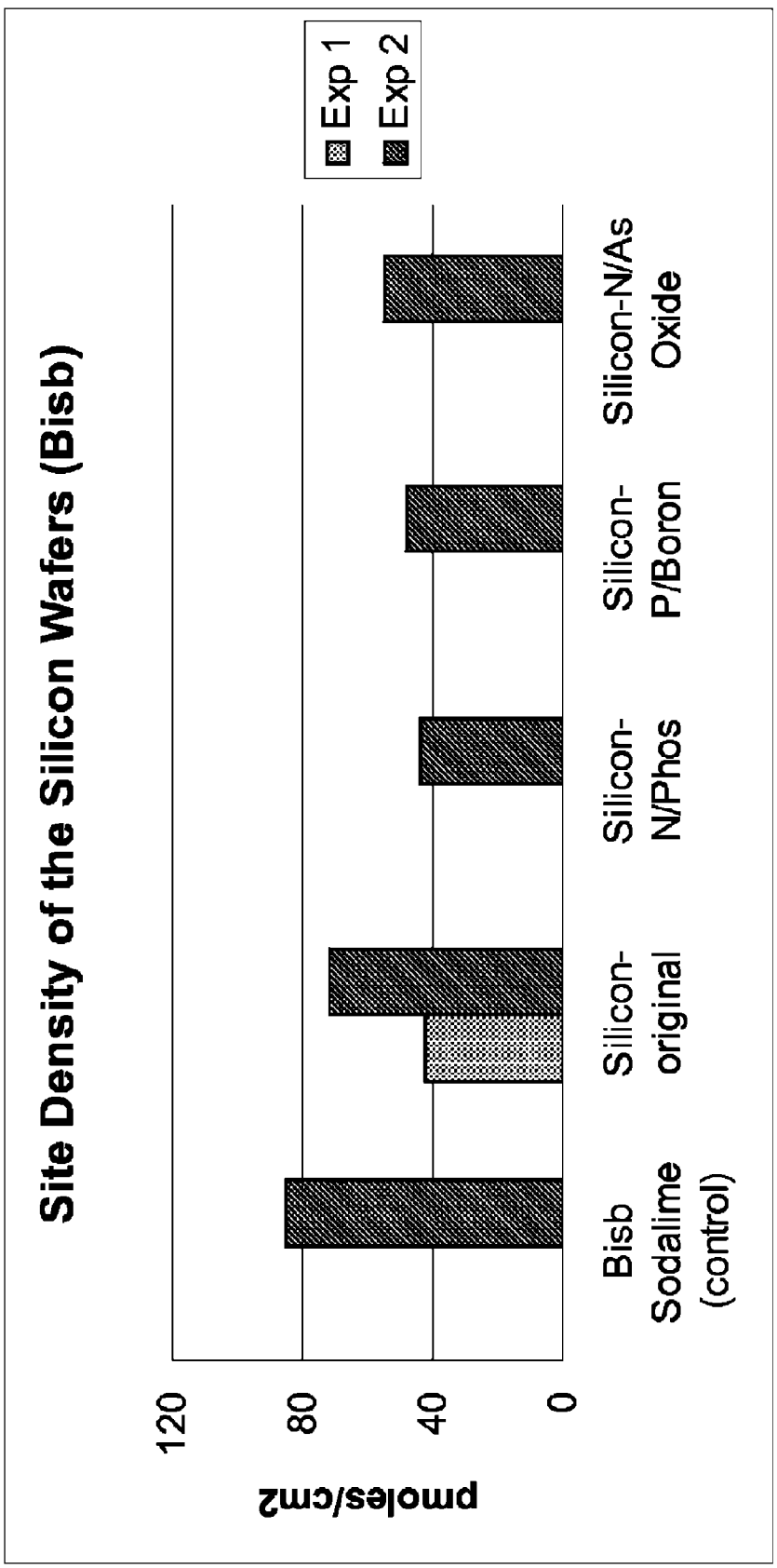
FIG. 1 depicts the site density of silicon wafers coated with N(2-hydroxyethyl)-N,N bis(trimethoxysilylpropyl)amine. The density of the silicon wafers was 2.33 g/cm.sup.3, and the thickness of the silicon wafers was approximately 400 to 700 µm.
Figure 2:
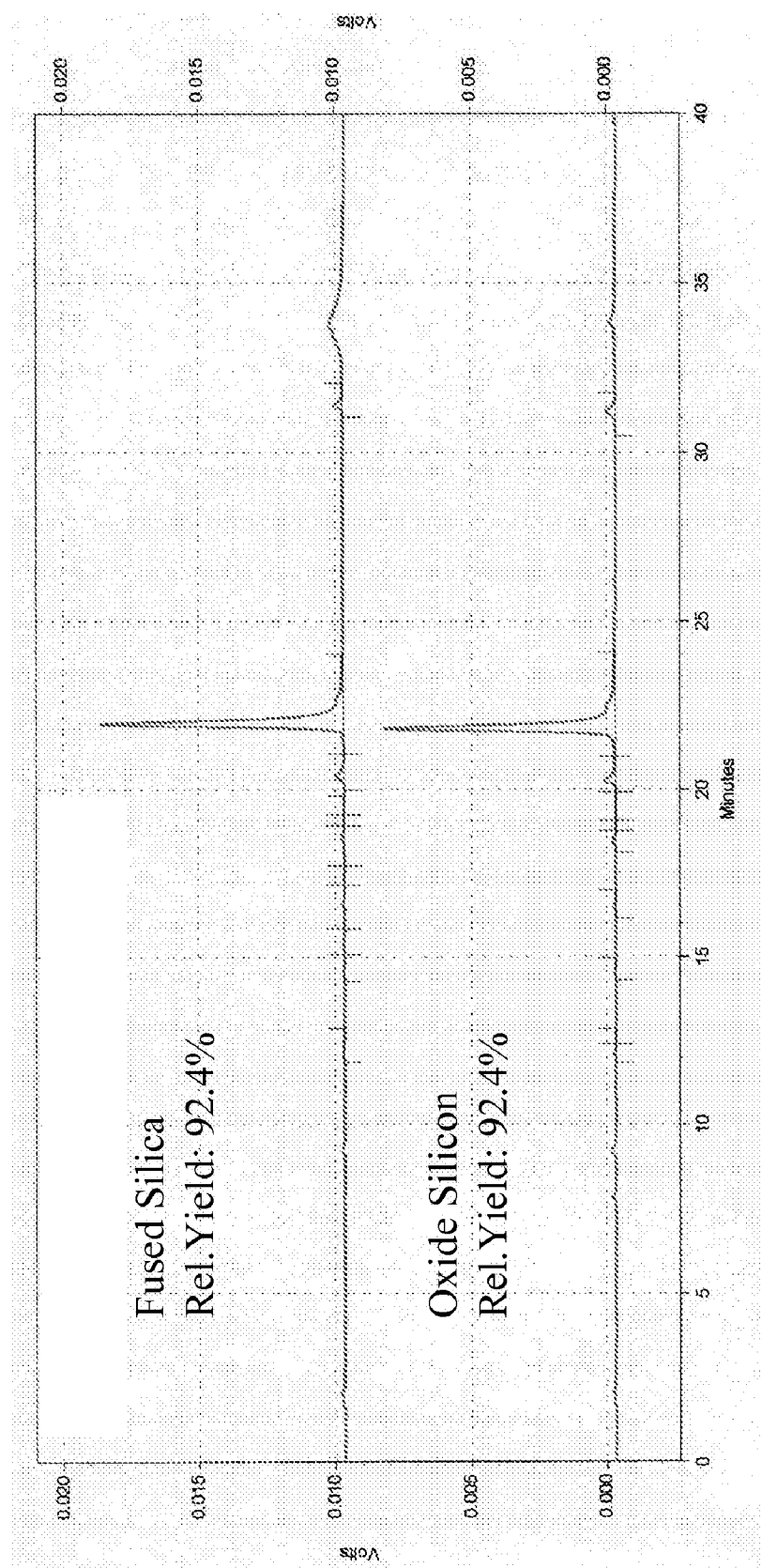
FIG. 2 depicts TCA 6-mers on fused silica and oxide silicone.
Figure 3:
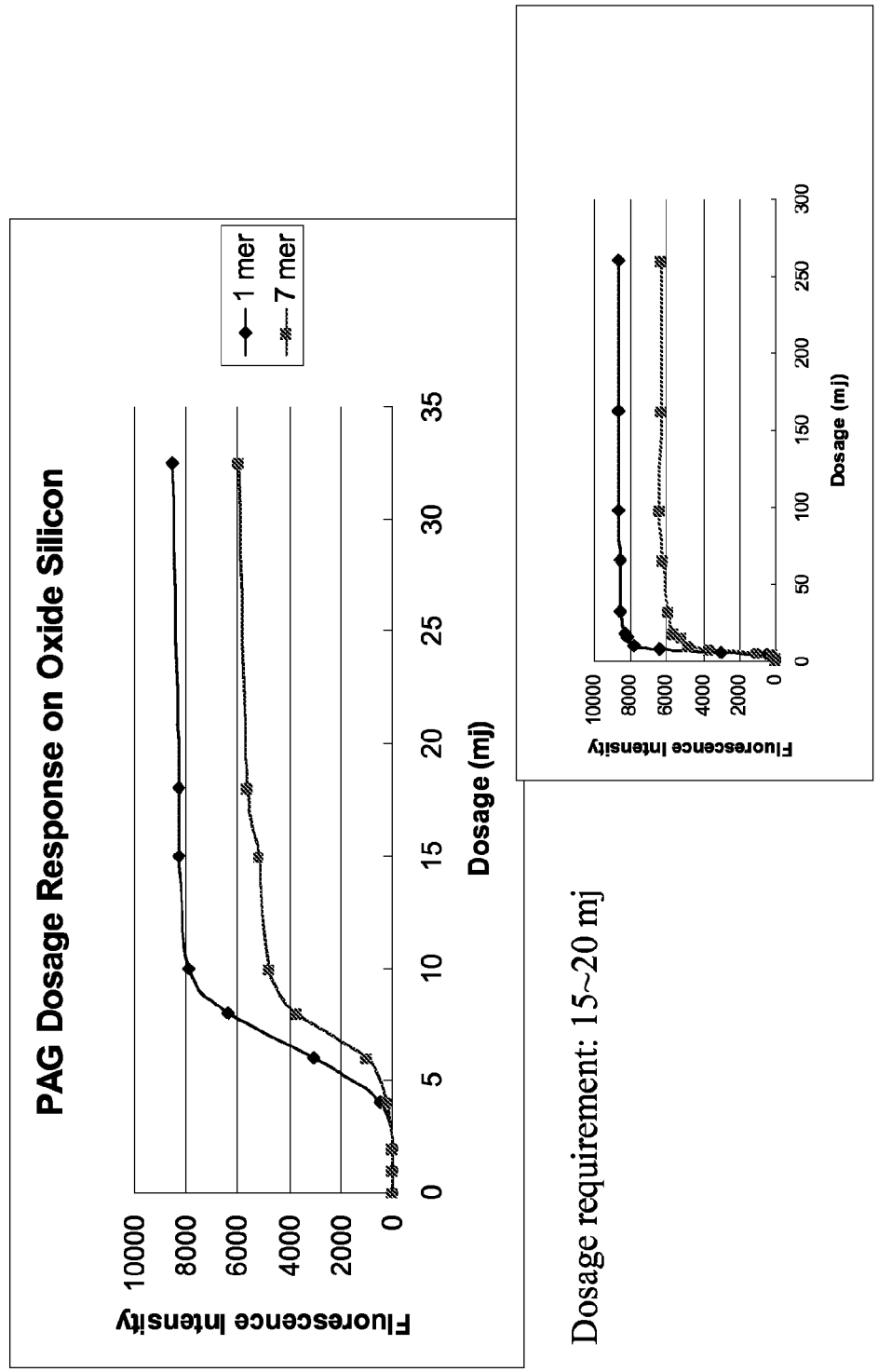
FIG. 3 depicts dosage response curves of a photoacid generator (PAG) on oxide silicon N(2-hydroxyethyl)-N,N bis (trimethoxysilylpropyl)amine.
Figure 4:
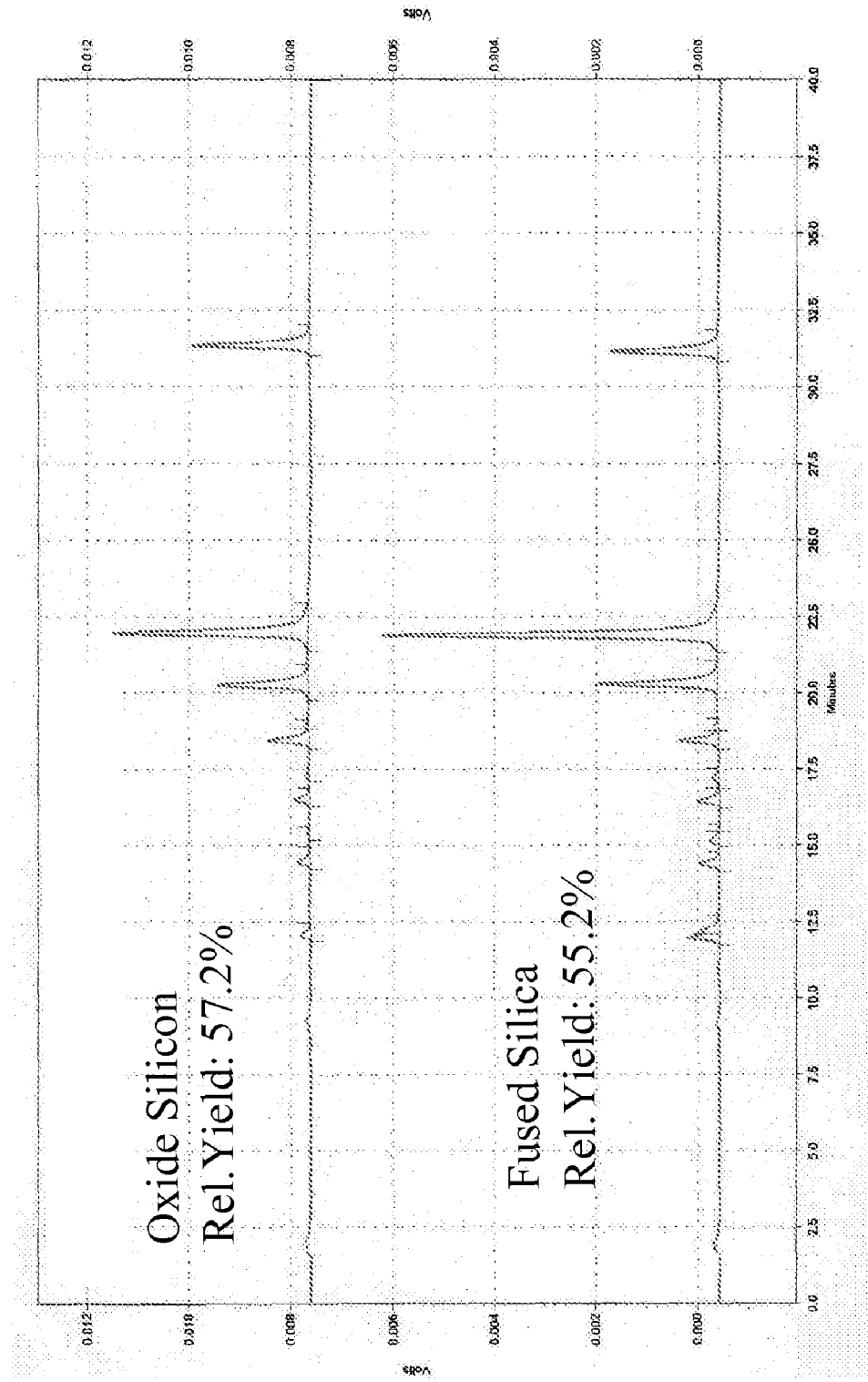
FIG. 4 depicts T-6-mers (PAG) with no base on oxide silicon and fused silica.
Figure 5:
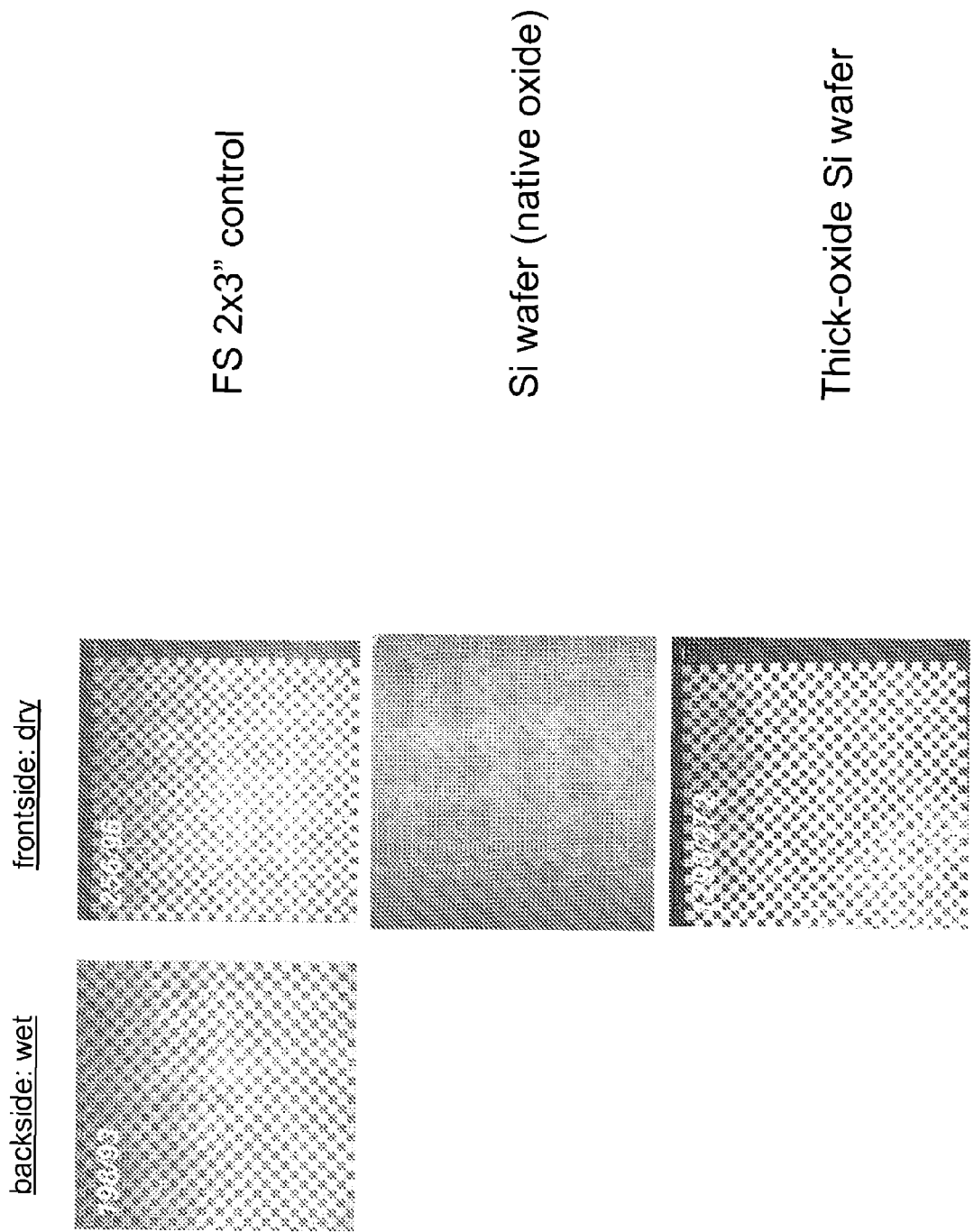
FIG. 5 depicts 100 mm Si wafer testing (N(2-hydroxyethyl)-N,N bis(trimethoxysilylpropyl)amine.) using Cy3 stain galvo scans.
Figure 6:
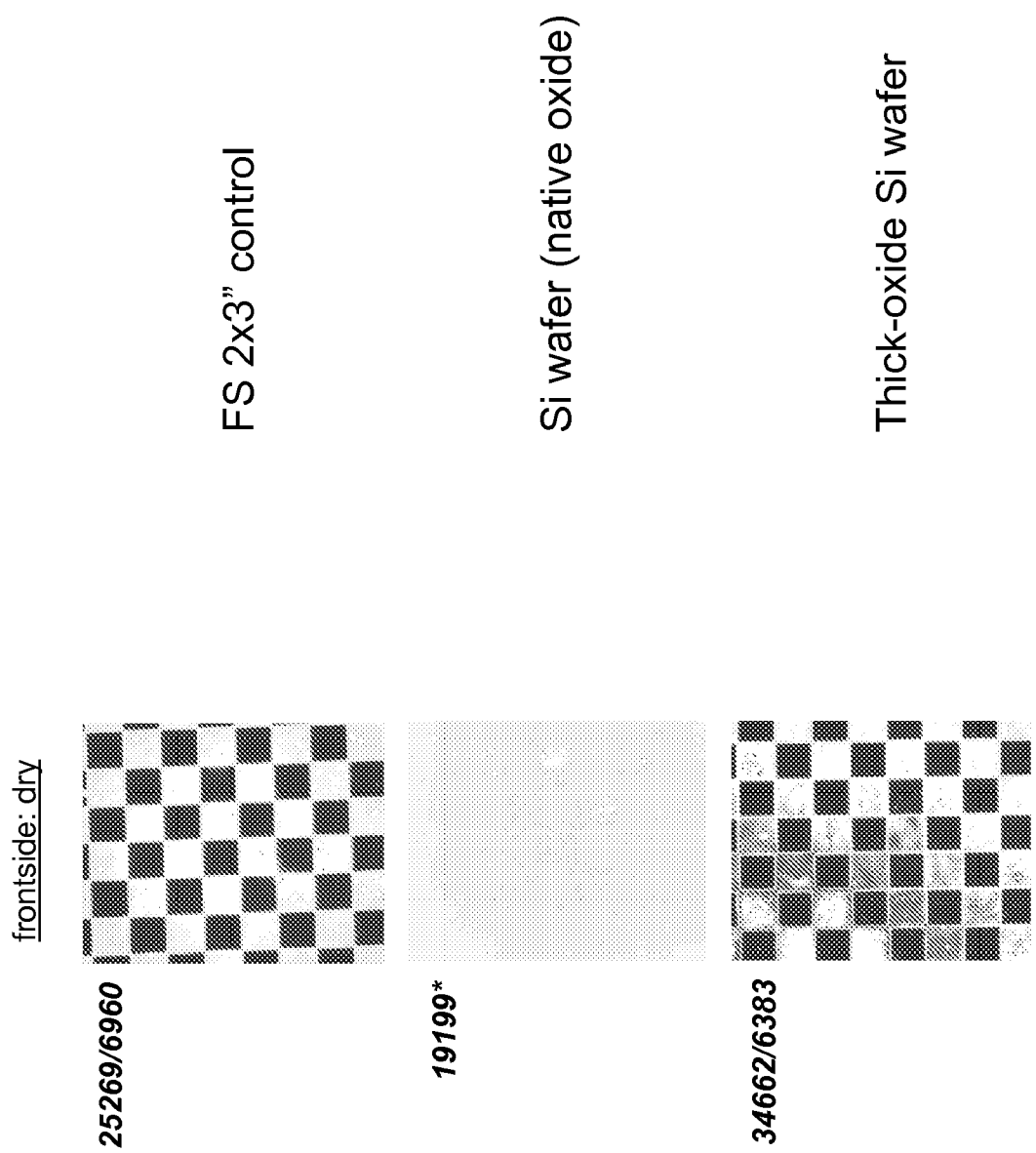
FIG. 6 depicts 100 mm Si wafer testing (N(2-hydroxyethyl)-N,N bis(trimethoxysilylpropyl)amine.) using Cy3 stain Axon scans.
Figure 7:
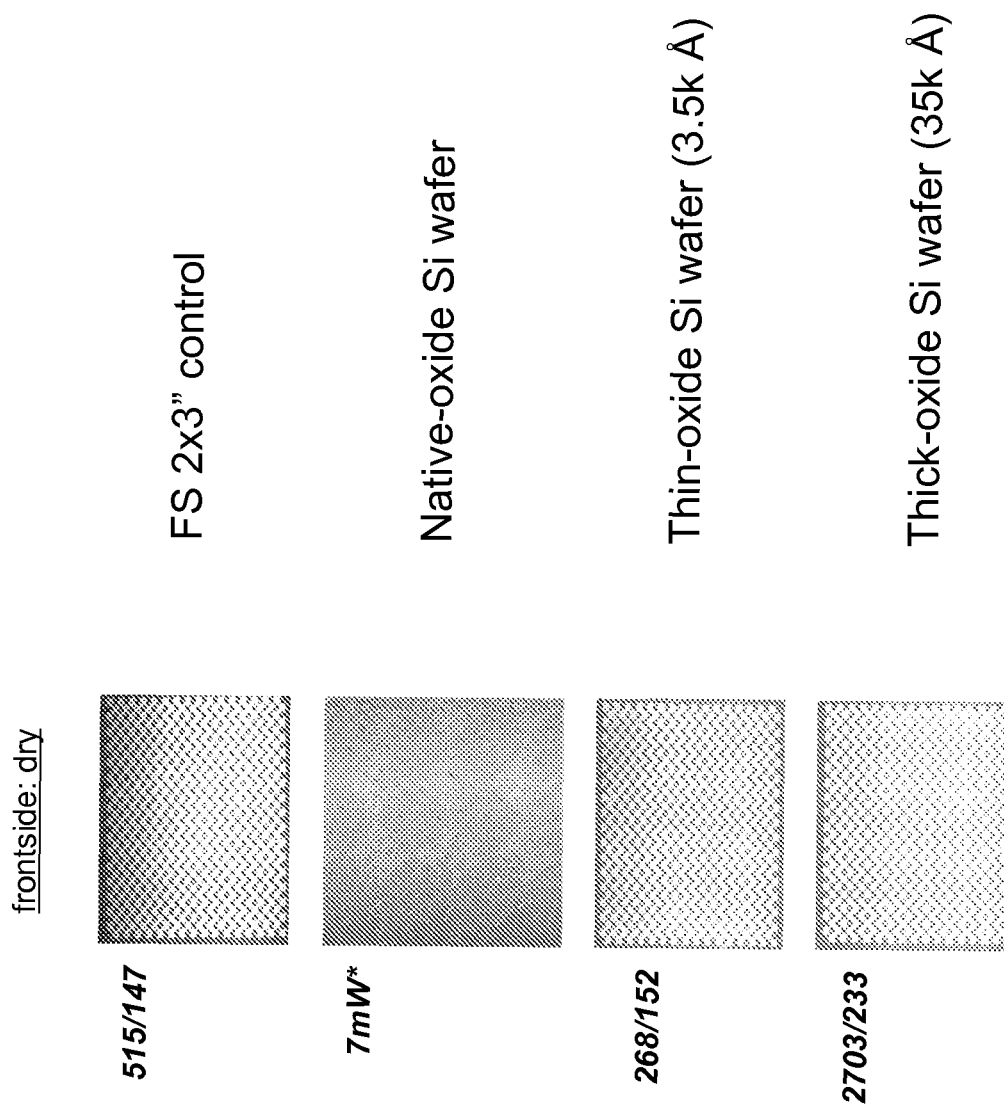
FIG. 7 depicts 100 mm Si wafer testing (N(2-hydroxyethyl)-N,N bis(trimethoxysilylpropyl)amine.) using Cy3 stain galvo scans showing oxide thickness.
Figure 8:
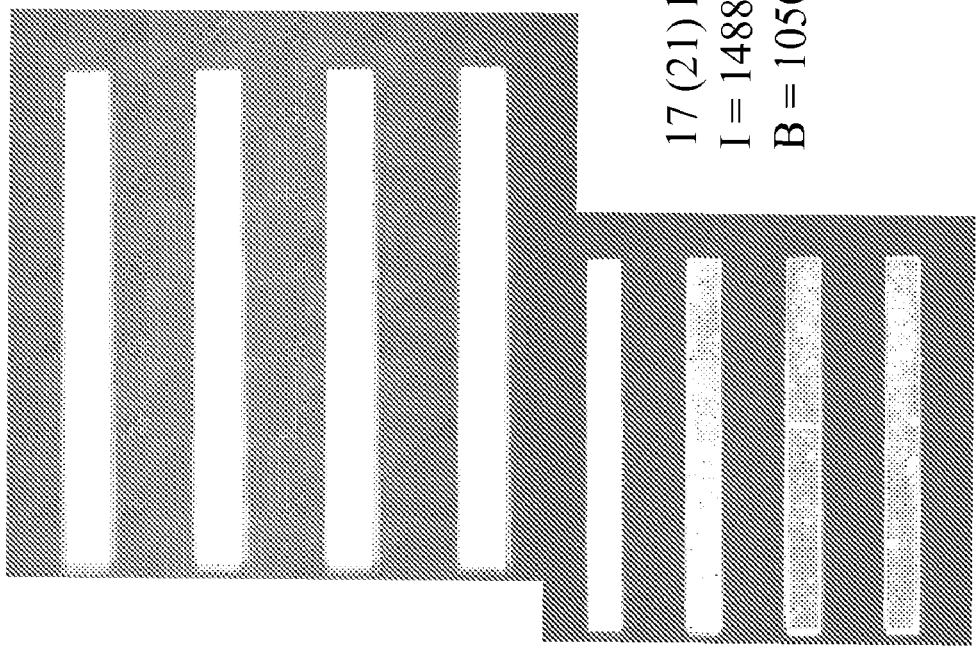
FIG. 8 depicts a 2 nM dual label target (N(2-hydroxyethyl)-N,N bis(trimethoxysilylpropyl)amine. oxide-Si substrate) fluorescein channel, front side scan.
Figure 8:
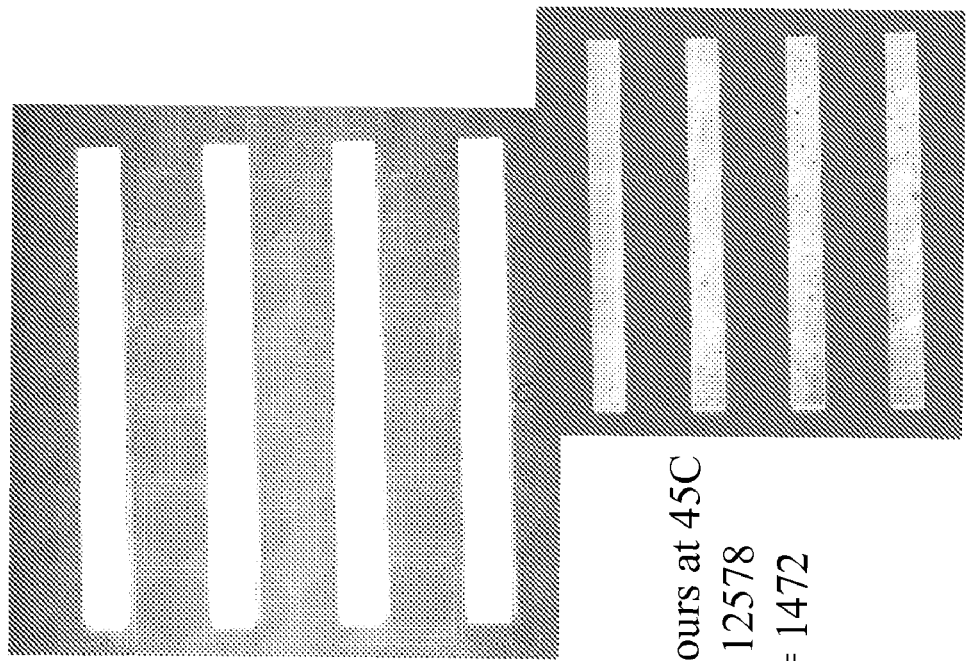
Figure 9:
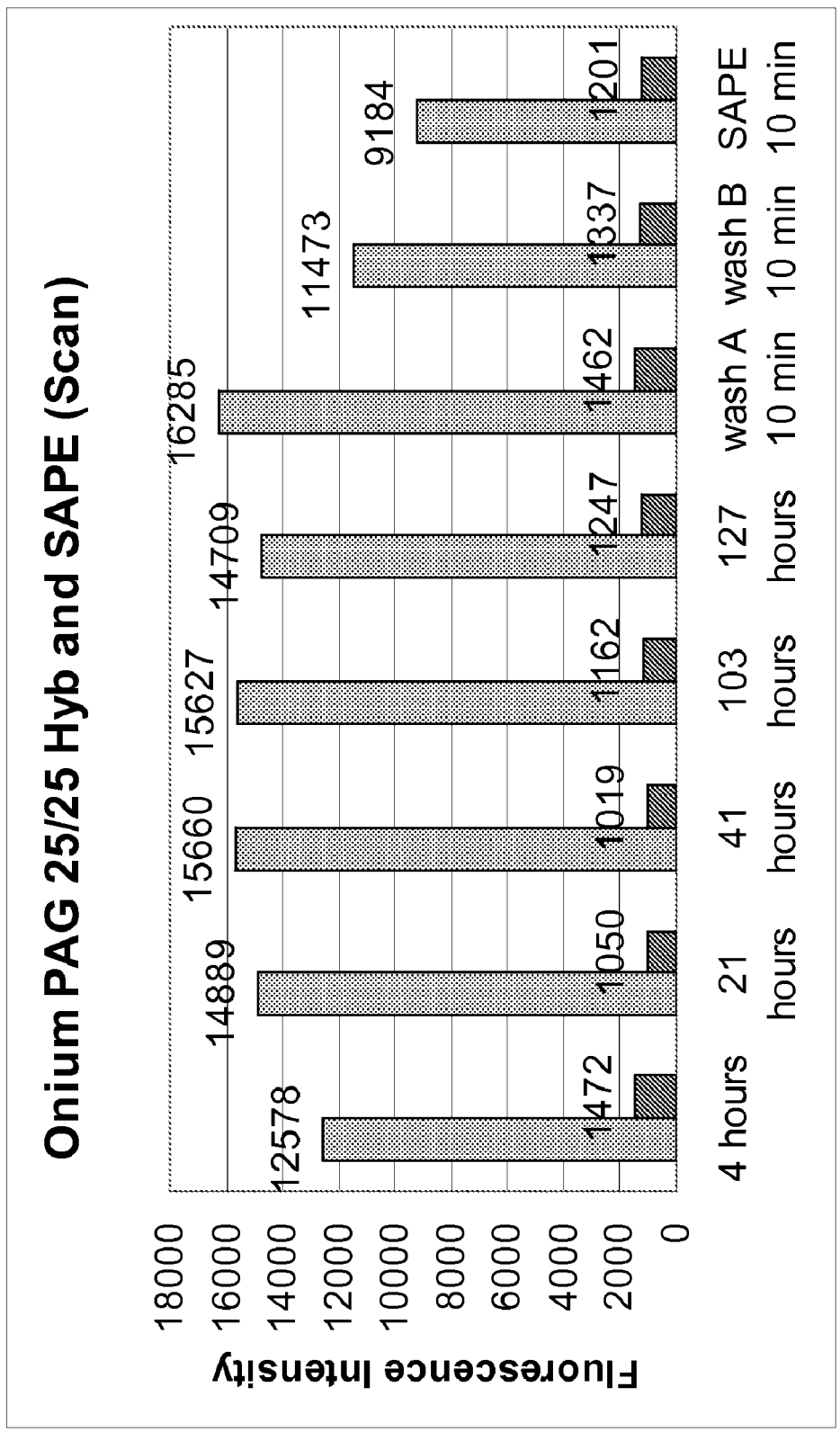
FIG. 9 depicts 100 mm Si wafer testing (N(2-hydroxyethyl)-N,N bis(trimethoxysilylpropyl)amine.) using MeNPOC hexamers. MeNPOC stepwise deprotection was reduced to 55% on native oxide. Other surfaces compared well to a fused-silica (FS) control, and, without intending to be bound by theory, each surface tested should produce good single-MeNPOC experiments.

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used herein, the singular forms "a," "an," and "the" include, but are not limited to, plural references unless the context clearly dictates otherwise. For example, the term "an agent" includes, but is not limited to, a plurality of agents, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5 and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry and immunology, which are within the skill of the art. Such conventional techniques include polymer array synthesis, hybridization, ligation, and detection of hybridization using a label. Specific illustrations of suitable techniques can be had by reference to the description provided below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual*, and *Molecular Cloning.: A Laboratory Manual* (all from Cold Spring Harbor Laboratory Press), Stryer, L. (1995) *Biochemistry* (4th Ed.) Freeman, New York, Gait, "Oligonucleotide Synthesis: A Practical Approach" 1984, IRL Press, London, Nelson and Cox (2000), *Lehninger, Principles of Biochemistry* 3rd Ed., W.H. Freeman Pub., New York, N.Y. and Berg et al. (2002) *Biochemistry*, 5th Ed., W.H. Freeman Pub., New York, N.Y., all of which are herein incorporated in their entirety by reference for all purposes.

The present invention can employ solid substrates, including arrays in certain embodiments. Methods and techniques applicable to polymer array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication No. WO 99/36760) and PCT/US01/04285 (International Publication No. WO 01/58593), each of which is incorporated herein by reference in its entirety for all purposes.

Patents that describe synthesis techniques in specific embodiments include U.S. Pat. Nos. 5,412,087, 6,147,205, 6,262,216, 6,310,189, 5,889,165 and 5,959,098, each of which is incorporated herein by reference in its entirety for all purposes. Nucleic acid arrays are described in many of the above patents, but the same techniques are applied to polypeptide arrays.

The present invention also contemplates many uses for polymers attached to solid substrates. These uses include gene expression monitoring, profiling, library screening, genotyping and diagnostics. Gene expression monitoring, and profiling methods can be shown in U.S. Pat. Nos. 5,800, 992, 6,013,449, 6,020,135, 6,033,860, 6,040,138, 6,177,248 and 6,309,822, which are all incorporated by reference in their entirety for all purposes. Genotyping and uses therefore are shown in U.S. Ser. Nos. 60/319,253, 10/013,598 (U.S. Patent Application Publication 20030036069), and U.S. Pat. Nos. 5,856,092, 6,300,063, 5,858,659, 6,284,460, 6,361,947, 6,368,799 and 6,333,179, which are incorporated by reference in their entirety for all purposes. Other uses are embodied in U.S. Pat. Nos. 5,871,928, 5,902,723, 6,045,996, 5,541, 061, and 6,197,506, which are incorporated by reference in their entirety for all purposes.

The present invention also contemplates sample preparation methods in certain preferred embodiments. Prior to or concurrent with genotyping, the genomic sample may be amplified by a variety of mechanisms, some of which may employ PCR. See, e.g., *PCR Technology: Principles and Applications for DNA Amplification* (Ed. H. A. Erlich, Freeman Press, NY, N.Y., 1992); *PCR Protocols. A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (Eds. McPherson et al., IRL Press, Oxford); and U.S. Pat. Nos. 4,683,202, 4,683,195, 4,800,159 4,965,188, and 5,333,675, each of which is incorporated herein by reference in its entirety for all purposes. The sample may be amplified on the array. See, for example, U.S. Pat. No. 6,300,070 and U.S. Ser. No. 09/513,300, which are incorporated herein by reference in their entirety for all purposes.

Other suitable amplification methods include the ligase chain reaction (LCR) (e.g., Wu and Wallace (1989) *Genomics* 4:560, Landegren et al. (1988) *Science* 241:1077 and Barringer et al. (1990) *Gene* 89:117), transcription amplification (Kwoh et al. (1989) *Proc. Natl. Acad. Sci. USA* 86:1173 and WO88/10315), self-sustained sequence replication (Guatelli et al. (1990) *Proc. Nat. Acad. Sci. USA,* 87:1874 and WO90/06995), selective amplification of target polynucleotide sequences (U.S. Pat. No 6,410,276), consensus sequence primed polymerase chain reaction (CP-PCR) (U.S. Pat. No. 4,437,975, arbitrarily primed polymerase chain reaction (AP-PCR) (U.S. Pat. Nos. 5,413,909, 5,861,245) and nucleic acid based sequence amplification (NABSA). Each of the above references is incorporated herein by reference in its entirety for all purposes. (See, U.S. Pat. Nos. 5,409,818, 5,554,517, and 6,063,603, each of which is incorporated herein by reference in its entirety for all purposes). Other amplification methods that may be used are described in, U.S. Pat. Nos. 5,242,794, 5,494,810, 4,988,617 and in U.S. Ser. No. 09/854,317. Each of the above references is incorporated herein by reference in its entirety.

Additional methods of sample preparation and techniques for reducing the complexity of a nucleic sample are described in Dong et al. (2001) *Genome Research* 11:1418, in U.S. Pat. No. 6,361,947, 6,391,592 and U.S. Ser. Nos. 09/916,135, 09/920,491 (U.S. Patent Application Publication 20030096235), Ser. No. 09/910,292 (U.S. Patent Application Publication 20030082543), and Ser. No. 10/013,598, each of which is incorporated herein by reference in its entirety.

Numerous methods for conducting polynucleotide hybridization assays have been well developed. Hybridization assay procedures and conditions will vary depending on the application and are selected in accordance with the general binding methods known including those referred to in: Maniatis et al. *Molecular Cloning. A Laboratory Manual* (2$^{nd}$ Ed. Cold Spring Harbor, N.Y., 1989); Berger and Kimmel *Methods in Enzymology*, Vol. 152, *Guide to Molecular Cloning Techniques* (Academic Press, Inc., San Diego, Calif., 1987); Young and Davism, *Proc. Natl. Acad. Sci. USA,* 80:1194 (1983). Methods and apparatus for carrying out repeated and controlled hybridization reactions have been described in U.S. Pat. Nos. 5,871,928, 5,874,219, 6,045,996 and 6,386,749, 6,391,623 each of which is hereby incorporated by reference in its entirety.

The present invention contemplates detection of hybridization between a ligand and its corresponding receptor by generation of specific signals. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 60/364,731 and in PCT Application PCT/US99/06097 (published as WO99/47964), each of which also is hereby incorporated by reference in its entirety. Each of these references is incorporated herein by reference in its entirety.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956; 6,025,601, 6,090,555, 6,141,096, 6,185,030, 6,201,639; 6,218,803; and 6,225,625, in U.S. Ser. No. 60/364,731 and in PCT Application PCT/US99/06097 (published as WO99/47964), each of which also is hereby incorporated by reference in its entirety.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Mcidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., 2$^{nd}$ ed., 2001). See U.S. Pat. No. 6,420,108. Each of these references is incorporated herein by reference in its entirety.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170. Each of these reference, is incorporated herein by reference in its entirety.

Light patterns can also be generated using Digital Micromirrors, Light Crystal on Silicon (LCOS), light valve arrays, laser beam patterns and other devices suitable for direct-write photolithography. See. e.g., U.S. Pat. Nos. 6,271,957 and 6,480,324, incorporated herein by reference in their entirety for all purposes.

Additionally, the present invention may have preferred embodiments that include methods for providing biological information over networks such as the internet as shown in U.S. Ser. Nos. 10/197,621, 10/063,559 (United States Publication No. 20020183936), Ser. Nos. 10/065,856, 10/065,868, 10/328,818, 10/328,872, 10/423,403, and 60/482,389, each of which is incorporated herein by reference in its entirety for all purposes.

The following definitions are used, unless otherwise described.

An "array," as defined herein, includes but is not limited to a preselected collection of different polymer sequences or probes which are associated with a surface of a substrate. An array may include polymers of a given length having all possible monomer sequences made up of a specific basis set of monomers, or a specific subset of such an array. For example, an array of all possible oligonucleotides of length 8 includes 65,536 different sequences. However, as noted above, an oligonucleotide array also may include only a subset of the complete set of probes. Similarly, a given array may exist on more than one separate substrate, e.g., where the number of sequences necessitates a larger surface area in order to include all of the desired polymer sequences.

A "functional group," as used herein, includes but is not limited to a reactive chemical moiety present on a given monomer, polymer or substrate surface. Examples of functional groups include, e.g., the 3' and 5' hydroxyl groups of nucleotides and nucleosides, as well as the reactive groups on the nucleobases of the nucleic acid monomers, e.g., the exocyclic amine group of guanosine, as well as amino and carboxyl groups on amino acid monomers.

A "monomer" or "building block," as used herein, includes but is not limited to a member of the set of smaller molecules which can be joined together to form a larger molecule or polymer. The set of monomers includes but is not restricted to, for example, the set of common L-amino acids, the set of D-amino acids, the set of natural or synthetic amino acids, the set of nucleotides (both ribonucleotides and deoxyribonucleotides, natural and unnatural) and the set of pentoses and hexoses. As used herein, monomer refers to any member of a basis set for synthesis of a larger molecule. A selected set of monomers forms a basis set of monomers. For example, the basis set of nucleotides includes A, T (or U), G and C. In another example, dimers of the 20 naturally occurring L-amino acids form a basis set of 400 monomers for synthesis of polypeptides. Different basis sets of monomers may be used in any of the successive steps in the synthesis of a polymer. Furthermore, each of the sets may include protected members which are modified after synthesis.

A "feature," as used herein, includes but is not limited to a selected region on a surface of a substrate in which a given polymer sequence is contained. Thus, where an array contains, e.g., 100,000 different positionally distinct polymer sequences on a single substrate, there will be 100,000 features.

An "edge," as used herein, includes but is not limited to a boundary between two features on a surface of a substrate. The sharpness of this edge, in terms of reduced bleed-over from one feature to another, is termed the "contrast" between the two features.

A "protecting group," as used herein, includes but is not limited to a material which is chemically bound to a reactive functional group on a monomer unit or polymer and which protective group may be removed upon selective exposure to an activator such as a chemical activator, or another activator, such as electromagnetic radiation or light, especially ultraviolet and visible light. Protecting groups that are removable upon exposure to electromagnetic radiation, and in particular light, are termed "photolabile protecting groups."

Halo is fluoro, chloro, bromo, or iodo. Alkyl, alkoxy, aralkyl, alkylaryl, and the like denote both straight and branched alkyl groups, but reference to an individual radical such as "propyl" embraces only the straight chain radical, a branched chain isomer such as "isopropyl" being specifically referred to. Aryl includes a phenyl radical or an ortho-fused, bicyclic, carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$—$C_4$)alkyl, phenyl or benzyl, as well as a radical of an ortho-fused, bicyclic heterocycle of about eight to ten ring atoms derived therefrom, particularly a benz-derivative or one derived by fusing a propylene, trimethylene or tetramethylene diradical thereto.

An "alkyl," as used herein, refers without limitation to a straight chain, branched or cyclic chemical groups containing only carbon and hydrogen. Alkyl groups include, without limitation, ethyl, propyl, butyl, pentyl, cyclopentyl and 2-methylbutyl. Alkyl groups are unsubstituted or substituted with one or more substituents (e.g., halogen, alkoxy, amino).

An "alkylene," as used herein, refers without limitation to a straight chain, branched or cyclic chemical group containing only carbon and hydrogen. Alkyl groups include, without limitation, ethylene, propylene, butylene, pentylene, and 2-methylbutylene. Alkyl groups are unsubstituted or substituted with one or more substituents (e.g., halogen, alkoxy, amino).

An "aryl," as used herein, refers without limitation to a monovalent, unsaturated, aromatic carbocyclic group. Aryl groups include, without limitation, phenyl, naphthyl, anthryl and biphenyl. Aryl groups are unsubstituted or substituted with 1 or more substituents (e.g. halogen, alkoxy, amino). "Arylene" refers to a divalent aryl group.

An "amido," as used herein, refers without limitation to a chemical group having the structure —C(O)$NR_3$—, wherein $R_3$ is hydrogen, alkyl or aryl. Preferably, the amido group is of the structure —C(O)$NR_3$— where D is hydrogen or alkyl having from about 1 to about 6 carbon atoms. More preferably, the amido alkyl group is of the structure —C(O)NH—.

An "alkanoyl," as used herein, refers without limitation to a chemical group having the structure —$(CH_2)_nC(O)$—, wherein n is an integer ranging from 0 to about 10. Preferably, the alkanoyl group is of the structure —$(CH_2)_nC(O)$—, wherein n is an integer ranging from about 2 to about 10. More preferably, the alkanoyl group is of the structure —$(CH_2)_nC(O)$—, wherein n is an integer ranging from about 2 to about 6. Most preferably, the alkanoyl group is of the structure —$CH_2C(O)$—.

An "alkyl amido," as used herein, refers without limitation to a chemical group having the structure —$R_4C(O)NR_3$—, wherein $R_3$ is hydrogen, alkyl or aryl, and $R_4$ is alkylene or arylene. Preferably, the alkyl amido group is of the structure —$(CH_2)_nC(O)NH$—, wherein n is an integer ranging from about 1 to about 10. More preferably, n is an integer ranging from about 1 to about 6. Most preferably, the alkyl amido group has the structure —$(CH_2)_2C(O)NH$— or the structure —$CH_2C(O)NH$—.

An "N-amido alkyl," as used herein, refers without limitation to a chemical group having the structure —C(O)$NR_3R_4$—, wherein $R_3$ is hydrogen, alkyl or aryl, and $R_4$ is alkylene or arylene. Preferably, the N-amido alkyl group is of the structure —C(O)$NH(CH_2)_nR_5$—, wherein n is an integer ranging from about 2 to about 10, and $R_5$ is O, $NR_6$, or C(O), and wherein $R_6$ is hydrogen, alkyl or aryl. More preferably, the N-amido alkyl group is of the structure —C(O)$NH(CH_2)_n$N(H)—, wherein n is an integer ranging from about 2 to about 6. Most preferably, the N-amido alkyl group is of the structure —C(O)$NH(CH_2)_4$N(H)—.

An "alkynyl alkyl," as used herein, refers without limitation to a chemical group having the structure —CC—$R_4$—, wherein $R_4$ is alkyl or aryl. Preferably, the alkynyl alkyl group is of the structure —CC—$(CH_2)_nR_5$—, wherein n is an integer ranging from 1 to about 10, and $R_5$ is O, $NR_6$ or C(O), wherein $R_6$ is hydrogen, alkyl or aryl. More preferably, the alkynyl alkyl group is of the structure —CC—$(CH_2)_n$N(H)—, wherein n is an integer ranging from 1 to about 4. Most preferably, the alkynyl alkyl group is of the structure —CC—$CH_2$N(H)—.

An "alkenyl alkyl," as used herein, refers without limitation to a chemical group having the structure —CH=CH—$R_4$—, wherein $R_4$ is a bond, alkyl or aryl. Preferably, the alkenyl alkyl group is of the structure —CH=CH—$(CH_2)$n$R_5$—, wherein n is an integer ranging from 0 to about 10, and $R_5$ is O, $NR_6$, C(O) or C(O)$NR_6$, wherein $R_6$ is hydrogen, alkyl or aryl. More preferably, the alkenyl alkyl group is of the structure —CH=CH—$(CH_2)_nC(O)NR_6$—, wherein n is an integer ranging from 0 to about 4. Most preferably, the alkenyl alkyl group is of the structure —CH=CH—C(O)N(H)—.

A "functionalized alkyl," as used herein, refers without limitation to a chemical group of the structure —$(CH_2)_nR_7$—, wherein n is an integer ranging from 1 to about 10, and $R_7$ is O, S, NH or C(O). Preferably, the functionalized alkyl group is of the structure —$(CH_2)_nC(O)$—, wherein n is an integer ranging from 1 to about 4. More preferably, the functionalized alkyl group is of the structure —$CH_2C(O)$—.

An "alkoxy," as used herein, refers without limitation to a chemical group of the structure —$O(CH_2)_nR_8$—, wherein n is an integer ranging from 2 to about 10, and $R_8$ is a bond, O, S, NH or C(O). Preferably, the alkoxy group is of the structure —$O(CH_2)n$, wherein n is an integer ranging from 2 to about 4. More preferably, the alkoxy group is of the structure —$OCH_2CH_2$—.

An "alkyl thio," as used herein, refers without limitation to a chemical group of the structure —$S(CH_2)_nR_8$—, wherein n is an integer ranging from 1 to about 10, and $R_8$ is a bond, O, S, NH or C(O). Preferably, the alkyl thio group is of the structure —$S(CH_2)_n$, wherein n is an integer ranging from 2 to about 4. More preferably, the thio group is of the structure —$SCH_2CH_2C(O)$—.

An "amino alkyl," as used herein, refers without limitation to a chemical group having an amino group attached to an alkyl group. Preferably an amino alkyl is of the structure —$(CH_2)_nNH$, wherein n is an integer ranging from about 2 to about 10. More preferably it is of the structure —$(CH_2)_nNH$—, wherein n is an integer ranging from about 2 to about 4. Most preferably, the amino alkyl group is of the structure —$(CH_2)_2NH$—.

The term "nucleic acid," as used herein, includes, but is not limited to, a polymer comprising two or more nucleotides and includes single-, double- and triple stranded polymers. As used herein, the term "nucleotide" refers without limitation to both naturally occurring and non-naturally occurring compounds and comprises a heterocyclic base, a sugar, and a linking group, preferably a phosphate ester. As used herein, the term "nucleoside" refers to both naturally occurring and non-naturally occurring compounds and comprises a heterocyclic base and a sugar.

Structural groups may be added to the ribosyl or deoxyribosyl unit of the nucleotide, such as a methyl or allyl group at the 2'-O position or a fluoro group that substitutes for the 2'-O group. The linking group, such as a phosphodiester, of the nucleic acid may be substituted or modified, for example with methyl phosphonates or O-methyl phosphates. Bases and sugars can also be modified, as is known in the art. "Nucleic acid," for the purposes of this disclosure, also includes "peptide nucleic acids" in which native or modified nucleic acid bases are attached to a polyamide backbone.

The term "oligonucleotide," sometimes referred to as "polynucleotide," includes, but is not limited to, a nucleic acid ranging from at least 5, 10, or 20 bases long and may be up to 20, 50, 100, 1,000, or 5,000 bases long and/or a compound that specifically hybridizes to a polynucleotide. Oligonucleotides of the present invention include sequences of deoxyribonucleic acid (DNA) or ribonucleic acid (RNA) and mimetics thereof which may be isolated from natural sources, recombinantly produced or artificially synthesized. A further example of a polynucleotide of the present invention is a peptide nucleic acid (PNA). See U.S. Pat. No. 6,156,501, incorporated herein by reference in its entirety for all purposes. The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The phrase "coupled to a support" includes, but is not limited to, being bound directly or indirectly thereto including attachment by covalent binding, hydrogen bonding, ionic interaction, hydrophobic interaction, or otherwise.

A "probe," as defined herein, includes but is not limited to a surface-immobilized molecule that is recognized by a particular target. These may also be referred to as ligands. Examples of probes encompassed by the scope of this invention include, but are not limited to, agonists and antagonists of cell surface receptors, toxins and venoms, viral epitopes, hormone receptors, peptides, peptidomimetics, enzymes, enzyme substrates, cofactors, drugs, lectins, sugars, oligonucleotides, nucleic acids, oligosaccharides, proteins or monoclonal antibodies, natural or modified, e.g., reshaped, chimeric, etc.

The terms "solid support," "support," and "substrate" as used herein are used interchangeably and include, but are not limited to, a material or group of materials having a rigid or semi-rigid surface or surfaces. In many embodiments, at least one surface of the solid support will be substantially flat or planar, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. Preferred substrates generally comprise planar crystalline substrates used in, e.g., the semiconductor and microprocessor industries, such as silicon, gallium arsenide and the like, or crystalline substrates such as silica based substrates (e.g. glass, quartz, or the like). These substrates are generally resistant to the variety of synthesis and analysis conditions to which they may be subjected. See U.S. Pat. No. 5,744,305 and U.S. Patent Appln. Pub. 20040105932, each of which is incorporated herein by reference in its entirety for all purposes, for exemplary substrates.

Individual planar substrates generally exist as wafers which can have varied dimensions. As used herein, the term "wafer" generally refers without limitation to a substantially flat sample of substrate from which a plurality of individual arrays or chips may be fabricated. The terms "array" or "chin" are used without limitation to refer to the final product of the individual array of polymer sequences, having a plurality of different positionally distinct polymer sequences coupled to the surface of the substrate. The size of a substrate wafer is generally defined by the number and nature of arrays that will be produced from the wafer. For example, more complex arrays, e.g., arrays having all possible polymer sequences produced from a basis set of monomers and having a given length, will generally utilize larger areas and thus employ larger substrates, whereas simpler arrays may employ smaller surface areas, and thus, less substrate.

In certain aspects of the invention, silicon wafers can be used to fabricate high-density arrays of oligonucleotides using the techniques described herein. Certain advanced lithography equipment (e.g., a stepper) is designed around the industry-standard round silicon wafer substrate. Commercially available substrates are typically 5, 6 and 8 inches in diameter. In contrast to fused silica, silicon wafers are thinner and non-transparent. The opacity of silicon requires that photochemistry and also scanning be performed "front side." A number of bulk physical proper-ties, such as crystal lattice orientation, dopant, resistivity and insulating oxide layer thickness have been discovered in accordance with the instant invention to not be critical to silanation or array synthesis. It was also discovered in accordance with the present invention that a variety of silicon substrates support silanation and non-photochemical methods of phosphoramidite-based probe synthesis with results comparable to fused silica. However, in accordance with the present invention, it has been discovered that effective confocal laser scanning has been found to be surprisingly dependent upon a suitable coating such as a layer of transparent oxide.

Typically, the substrate wafer will range in size of from about 1"×1" to about 12"×12", and will have a thickness of from about 0.5 mm to about 5 mm. Individual substrate segments which include the individual arrays, or in some cases a desired collection of arrays, are typically much smaller than the wafers, measuring from about 0.2 cm.×0.2 cm to about 5 cm×5 cm. In particularly preferred aspects, the substrate wafer is about 5"×5" whereas the substrate segment is approximately 1.28 cm×1.28 cm. Although a wafer can be used to fabricate a single large substrate segment, typically, a large number of substrate segments will be prepared from a single wafer. For example, a wafer that is 5"×5" can be used to fabricate upwards of 49 separate 1.28 cm×1.28 cm substrate segments. The number of segments prepared from a single wafer will generally vary depending upon the complexity of the array, and the desired feature size.

Although primarily described in terms of flat or planar substrates, the present invention may also be practiced with substrates having substantially different conformations. For example, the substrate may exist as particles, strands, precipitates, gels, sheets, tubing, spheres, containers, capillaries, pads, slices, films, plates, slides, and the like. In a preferred alternate embodiment, the substrate is a glass tube or microcapillary. The capillary substrate provides advantages of higher surface area to volume ratios, reducing the amount of reagents necessary for synthesis. Similarly, the higher surface to volume ratio of these capillary substrates imparts more efficient thermal transfer properties. Additionally, preparation of the polymer arrays may be simplified through the use of these capillary based substrates. For example, minimizing differences between the regions on the array, or "cells," and their "neighboring cells" is simplified in that there are only two neighboring cells for any given cell (see discussion below for edge minimization in chip design). Spatial separation of two neighboring cells on an array merely involves the incorporation of a single blank cell, as opposed to full blank lanes as generally used in a flat substrate conformation. This substantially conserves the surface area available for polymer synthesis. Manufacturing design may also be simplified by the linear nature of the substrate. In particular, the linear substrate may be moved down a single mask in a direction perpendicular to the length of the capillary. As it is moved, the capillary will encounter linear reticles (translucent regions of the mask), one at a time, thereby exposing selected regions within the capillary or capillary. This can allow bundling of parallel capillaries during synthesis wherein the capillaries are exposed to thicker linear reticles, simultaneously, for a batch processing mode, or individual capillaries may be placed on a mask having all of the linear reticles lined up so that the capillary can be stepped down the mask in one direction. Subsequent capillaries may be stepped down the mask at least one step behind the previous capillary. This employs an assembly line structure to the substrate preparation process.

As an example, a standard optimization chip for detecting 36 simultaneous mutations using a flat geometry chip and an optimization tiling strategy, is 44×45 features (1980 probes and blanks), with 36 blocks of 40 probes each (1440 probes), plus 15 blanks per block (540 blank probes). A capillary format, however, can incorporate the same number of test probes in a smaller space. Specifically, in a capillary substrate, 36 strings of 40 probes will have only one blank space separating each probe group (35 blank probes), for a total of 1475 features.

Finally, linear capillary based substrates can provide the advantage of reduced volume over flat geometries. In particular, typical capillary substrates have a volume in the 1-10 μl range, whereas typical flow cells for synthesizing or screening flat geometry chips have volumes in the range of 100 μl.

A. Stripping and Rinsing

In one aspect of the present invention, oxide-coated wafers are silanated as supplied from the wafer vendor without prior stripping. In other aspects, in order to ensure maximum efficiency and accuracy in synthesizing polymer arrays, it is desirable to provide a clean substrate surface upon which the various reactions are to take place. Accordingly, in some processing embodiments of the present invention, the substrate is stripped to remove any residual dirt, oils or other fluorescent materials which may interfere with the synthesis reactions, or subsequent analytical use of the array.

The process of stripping the substrate typically involves applying, immersing or otherwise contacting the substrate with a stripping solution. Stripping solutions may be selected from a number of commercially available, or readily prepared chemical solutions used for the removal of dirt and oils, which solutions are well known in the art. Particularly preferred stripping solutions are composed of a mixture of concentrated $H_2SO_4$ and $H_2O_2$. Such solutions are generally available from commercial sources, e.g., NANOSTRIP™ from Cyantek Corp. (Fremont, Calif.). After stripping, rinsed with water and in preferred aspects, is then contacted with a solution of NaOH, which results in regeneration of an even layer of hydroxyl functional groups on the surface of the substrate. In this case, the substrate is again rinsed with water, followed by a rinse with HCl to neutralize any remaining base, followed again by a water rinse. The various stripping and rinsing steps may generally be carried out using a spin-rinse-drying apparatus of the type generally used in the semiconductor manufacturing industry.

Gas phase cleaning and preparation methods may also be applied to the substrate wafers using, e.g., $H_2O$ or $O_2$ plasma or reactive ion etching (RIE) techniques that are well known in the art.

B. Coating Layer

Embodiments of the present invention are based on the unexpected finding that there is a strong correlation between array signal detection and oxide layer thickness. In accordance with a preferred embodiment, silicon wafers coated with a coating layer, e.g., an oxide layer, are used as substrates for array synthesis and subsequent fluorescence analysis. An oxide layer can be composed of conventional oxide materials such as silicon oxide (SiO), silicon dioxide ($SiO_2$), borophosphosilicate glass (BPSG), borosilicate glass (BSG), fluorosilicate glass (FSG), tetraethoxysilane (TEOS), and the like. Oxide layers are described in U.S. Pat. No. 6,191,046, incorporated herein by reference in its entirety for all purposes.

In a certain embodiments, the coating layer, e.g., an oxide layer, has a thickness of approximately at least 3,500 angstroms, 4,000 angstroms, 4,500 angstroms, 5,000 angstroms, 5,500 angstroms, 6,000 angstroms, 6,500 angstroms, 7,000 angstroms, 7,500 angstroms, 8,000 angstroms, 8,500 angstroms, 9,000 angstroms, 9,500 angstroms, 10,000 angstroms, 11,000 angstroms, 12,000 angstroms, 13,000 angstroms, 14,000 angstroms, 15,000 angstroms, 16,000 angstroms, 17,000 angstroms, 18,000 angstroms, 19,000 angstroms, 20,000 angstroms, 21,000 angstroms, 22,000 angstroms, 23,000 angstroms, 24,000 angstroms, 25,000 angstroms, 26,000 angstroms, 27,000 angstroms, 28,000 angstroms, 29,000 angstroms, 30,000 angstroms, 40,000 angstroms, 45,000 angstroms, 50,000 angstroms, 55,000 angstroms, 60,000 angstroms, 65,000 angstroms, 70,000 angstroms, 75,000 angstroms, 80,000 angstroms, 85,000 angstroms, 90,000 angstroms, 95,000 angstroms, 100,000 angstroms, or more. In a preferred embodiment, a coating layer (e.g., an oxide layer) is approximately at least 3,500 angstroms thick. In a particularly preferred embodiment, a coating layer (e.g., an oxide layer) is approximately at least 35,000 angstroms thick.

In accordance with preferred aspects of the present invention, it is contemplated that antireflective or adsorptive coatings can substitute for an oxide coating to attain a robust fluorescence signal. Antireflective and/or adsorptive coatings are known in the art and described in U.S. Pat. No. 6,156,149, incorporated herein by reference in its entirety for all purposes.

In certain aspects of the invention, a coating comprising a silicon compound can be added to the substrates described herein. Such coatings can be added to the substrate itself or to another coating layer. Suitable silicon compounds are described in U.S. Patent Appl. Pub. No. 20010027187, incorporated herein by reference in its entirety for all purposes.

The use of a fluorophore in front of a reflecting surface and the resulting interaction of standing waves as a function of the distance to the reflector and the wavelength(s) of light is described in Lambacher and Fromherz (1996) *Appl. Phys. A* 63:207; Braun and Fromherz (1997) *Appl. Phys. A* 65:341; Braun and Fromherz (1998) *Phys. Rev. Lett.* 81:5241; and Drexhage (1974) *Prog. In Optics* XII:163, each of which is incorporated herein by reference in its entirety for all purposes.

C. Derivatization

Following the optional step of cleaning and stripping of the substrate surface and the addition of a coating layer, the surface is derivatized to provide sites or functional groups on the substrate surface for synthesizing the various polymer sequences on that surface. In particular, derivatization provides reactive functional groups, e.g., hydroxyl, carboxyl, amino groups or the like, to which the first monomers in the polymer sequence may be attached. In preferred aspects, the substrate surface is derivatized using silane in either water or ethanol. Preferred silanes include mono- and dihydroxyalkylsilanes, which provide a hydroxyl functional group on the surface of the substrate. Also preferred are aminoalkyltrialkoxysilanes which can be used to provide the initial surface modification with a reactive amine functional group. Particularly preferred are 3-aminopropyltriethoxysilane and 3-aminopropyltrimethoxysilane ("APS"). Derivatization of the substrate using these latter amino silanes provides a linkage that is stable under synthesis conditions and final deprotection conditions (for oligonucleotide synthesis, this linkage is typically a phosphoramidate linkage, as compared to the phosphodiester linkage where hydroxyalkylsilanes are used). Additionally, this amino silane derivatization provides several advantages over derivatization with hydroxyalkylsilanes. For example, the aminoalkyltrialkoxysilanes are inexpensive and can be obtained commercially in high purity from a variety of sources, the resulting primary and secondary amine functional groups are more reactive nucleophiles than hydroxyl groups, the aminoalkyltrialkoxysilanes are less prone to polymerization during storage, and they are sufficiently volatile to allow application in a gas phase in a controlled vapor deposition process.

Additionally, silanes can be prepared having protected or "masked" hydroxyl groups and which possess significant volatility. As such, these silanes can be readily purified by, e.g., distillation, and can be readily employed in gas-phase deposition methods of silanating substrate surfaces. After coating these silanes onto the surface of the substrate, the hydroxyl groups may be deprotected with a brief chemical treatment, e.g., dilute acid or base, which will not attack the substrate-silane bond, so that the substrate can then be used for polymer synthesis. Examples of such silanes include acetoxyalkylsilanes, such as acetoxyethyltrichlorosilane, acetoxypropyltrimethoxysilane, which may be deprotected after application using, e.g., vapor phase ammonia and methylamine or liquid phase aqueous or ethanolic ammonia and alkylamines. Epoxyalkylsilanes may also be used, such as glycidoxypropyltrimethoxysilane which may be deprotected using, e.g., vapor phase HCl, trifluoroacetic acid or the like, or liquid phase dilute HCl.

The physical operation of silanation of the substrate generally involves dipping or otherwise immersing the substrate in the silane solution. Following immersion, the substrate is generally spun as described for the substrate stripping process, i.e., laterally, to provide a uniform distribution of the silane solution across the surface of the substrate. This ensures a more even distribution of reactive functional groups on the surface of the substrate. Following application of the silane layer, the silanated substrate may be baked to polymerize the silanes on the surface of the substrate and improve the reaction between the silane reagent and the substrate surface. Baking typically takes place at temperatures in the range of from 90° C. to 120° C., with 110° C. being most preferred, for a time period of from about 1 minute to about 10 minutes, with 5 minutes being preferred.

In alternative aspects, as noted above, the silane solution may be contacted with the surface of the substrate using controlled vapor deposition methods or spray methods. These methods involve the volatilization or atomization of the silane solution into a gas phase or spray, followed by deposition of the gas phase or spray upon the surface of the substrate, usually by ambient exposure of the surface of the substrate to the gas phase or spray. Vapor deposition typically results in a more even application of the derivatization solution than simply immersing the substrate into the solution.

The efficacy of the derivatization process, e.g., the density and uniformity of functional groups on the substrate surface, may generally be assessed by adding a fluorophore which binds the reactive groups, e.g., a fluorescent phosphoramidite such as FLUOREPRIME™ from Pfizer Inc. (New York, N.Y.), FLUOREDITE™ from Millipore Corp. (Billerica, Mass.) or FAM, and ascertaining the relative fluorescence across the surface of the substrate.

D. Synthesis

General methods for the solid phase synthesis of a variety of polymer types have been previously described. Methods of synthesizing arrays of large numbers of polymer sequences, including oligonucleotides and peptides, on a single substrate have also been described. See U.S. Pat Nos. 5,143,854 and 5,384,261 and Published PCT Application No WO 92/10092, each of which is incorporated herein by reference in its entirety for all purposes.

The synthesis of oligonucleotides on the surface of a substrate can be carried out using light directed methods as described in, e.g., U.S. Pat. Nos. 5,143,854 and 5,384,261 and Published PCT Application No WO 92/10092, or mechanical synthesis methods as described in U.S. Pat. No. 5,384,261 and Published PCT Application No. 93/09668, each of which is incorporated herein by reference in its entirety for all purposes. In preferred embodiments, photochemical steps, and in particular photoacid generator (PAG) synthesis techniques are preformed "front side" on a substrate having a front side and a back side. In particular, these light-directed or photolithographic synthesis methods involve a photolysis step and a chemistry step. The substrate surface, prepared as described herein, comprises functional groups on its surface. These functional groups are protected by photolabile protecting groups, i.e., "photoprotected," also as described herein. During the photolysis step, portions of the surface of the substrate are exposed to light or other activators to activate the functional groups within those portions, i.e., to remove photoprotecting groups. The substrate is then subjected to a chemistry step in which chemical monomers that are photoprotected at one or more functional groups are then contacted with the surface of the substrate. These monomers bind to the activated portion of the substrate through an unprotected functional group.

Subsequent activation and coupling steps couple monomers to other preselected regions, which may overlap with all or part of the first region. The activation and coupling sequence at each region on the substrate determines the sequence of the polymer synthesized thereon. In particular, light is shown through the photolithographic masks which are designed and selected to expose and thereby activate a first particular preselected portion of the substrate. Monomers are then coupled to all or part of this portion of the substrate. The masks used and monomers coupled in each step can be selected to produce arrays of polymers having a range of desired sequences, each sequence being coupled to a distinct spatial location on the substrate which location also dictates the polymer's sequence. The photolysis steps and chemistry steps are repeated until the desired sequences have been synthesized upon the surface of the substrate.

Basic strategy for light directed synthesis of oligonucleotides on a VLSIPS™ Array is described in U.S. Patent Appl. Pub. No. 20040105932, incorporated herein by reference in its entirety for all purposes. Briefly, the surface of a substrate or solid support, modified with photosensitive protecting groups is illuminated through a photolithographic mask, yielding reactive hydroxyl groups in the illuminated regions. A selected nucleotide, typically in the form of a 3'-O-phosphoramidite-activated deoxynucleoside (protected at the 5' hydroxyl with a photosensitive protecting group), is then presented to the surface and coupling occurs at the sites that were exposed to light. Following capping and oxidation, the substrate is rinsed and the surface is illuminated through a second mask, to expose additional hydroxyl groups for coupling. A second selected nucleotide (e.g., 5'-protected, 3'-O-phosphoramidite-activated deoxynucleoside) is presented to the surface. The selective deprotection and coupling cycles are repeated until the desired set of products is obtained (Pease et al. (1994) *Proc. Natl. Acad. Sci. USA* 91:5022, incorporated herein by reference in its entirety for all purposes. Since photolithography is used, the process can be readily miniaturized to generate high density arrays of oligonucleotide probes. Furthermore, the sequence of the oligonucleotides at each site is known. Such photolithographic methods are also described in U.S. Pat. Nos. 5,143,854 and 5,489,678 and Published PCT Application No. WO 94/10128 each of which is incorporated herein by reference in its entirety for all purposes. In the large scale processes of the present invention, it is typically preferred to utilize photolithographic synthesis methods.

Using the above described methods, arrays may be prepared having all polymer sequences of a given length which are composed of a basis set of monomers. Such an array of oligonucleotides, made up of the basis set of four nucleotides, for example, would contain up to $4^n$ oligonucleotides on its surface, where n is the desired length of the oligonucleotide probe. For an array of 8-mer or 10-mer oligonucleotides, such arrays could have upwards of about 65,536 and 1,048,576 different oligonucleotides, respectively. Generally, where it is desired to produce arrays having all possible polymers of length n, a simple binary masking strategy can be used, as described in U.S. Pat. No. 5,143,854, incorporated herein by reference in its entirety for all purposes.

Alternate masking strategies can produce arrays of probes which contain a subset of polymer sequences, i.e., polymers having a given subsequence of monomers, but are systematically substituted at each position with each member of the basis set of monomers. In the context of oligonucleotide probes, these alternate synthesis strategies may be used to lay down or "tile" a range of probes that are complementary to, and span the length of a given known nucleic acid segment. The tiling strategy will also include substitution of one or more individual positions within the sequence of each of the probe groups with each member of the basis set of nucleotides. These positions are termed "interrogation positions." By reading the hybridization pattern of the target nucleic acid, one can determine if and where any mutations lie in the sequence, and also determine what the specific mutation is by identifying which base is contained within the interrogation position. Tiling methods and strategies are discussed in substantial detail in U.S. patent application Ser. No. 08/143,312 filed Oct. 26, 1993, and incorporated herein by reference in its entirety for all purposes.

Tiled arrays may be used for a variety of applications, such as identifying mutations within a known oligonucleotide sequence or "target." Specifically, the probes on the array will have a subsequence which is complementary to a known nucleic acid sequence, but wherein at least one position in that sequence has been systematically substituted with the other three nucleotides.

Use of photolabile protecting groups during polymer synthesis has been previously reported, as described above. Preferred photolabile protecting groups generally have the following characteristics: they prevent selected reagents from modifying the group to which they are attached; they are stable to synthesis reaction conditions (that is, they remain attached to the molecule); they are removable under conditions that minimize potential adverse effects upon the structure to which they are attached; and, once removed, they do not react appreciably with the surface or surface bound oligomer. In some embodiments, liberated byproducts of the photolysis reaction can be rendered non-reactive toward the growing oligomer by adding a reagent that specifically reacts with the byproduct.

The removal rate of the photolabile protecting groups generally depends upon the wavelength and intensity of the incident radiation, as well as the physical and chemical properties of the protecting group itself. Preferred protecting groups are removed at a faster rate and with a lower intensity of radiation. Generally, photoprotecting groups that undergo photolysis at wavelengths in the range from 300 nm to approximately 450 nm are preferred.

Generally, photolabile or photosensitive protecting groups include ortho-nitrobenzyl and ortho-nitrobenzyloxycarbonyl protecting groups. The use of these protecting groups has been proposed for use in photolithography for electronic device fabrication (see, e.g., Reichmanis et al. (1985) *J. Polymer Sci. Polymer Chem. Ed.* 23:1, incorporated herein by reference in its entirety for all purposes).

Examples of additional photosensitive protecting groups which may be used in the light directed synthesis methods herein described, include, e.g., 1-pyrenylmethyloxycarbonyl, α,α-dimethyl-3,5-dimethoxybenzyloxycarbonyl, 4-methoxyphenacyloxycarbonyl, 3'-methoxybenzoinyloxycarbonyl, 3',5'-dimethoxybenzoinyloxycarbonyl 2',3'-dimethoxybenzoinyloxycarbonyl, 2',3'-(methylenedioxy)benzoinyloxycarbonyl, N-(5-bromo-7-nitroindolinyl)carbonyl 3,5-dimethoxybenzyloxycarbony-1,α-(2-methylene-anthraquinone)oxycarbonyl and the like.

Particularly preferred photolabile protecting groups for protection of either the 3' or 5'-hydroxyl-groups of nucleotides or nucleic acid polymers include the o-nitrobenzyl protecting groups described in Published PCT Application No. WO 92/10092, incorporated herein by reference in its entirety for all purposes. These photolabile protecting groups include, e.g., (2-nitro-naphthalen-1-yl)-phenylmethylcarbonyl (NNPOC), 94'-methoxy-3-nitro-biphenyl-4-yl)-phenylmethylcarbonyl (MBPMOC), nitroveratryloxycarbonyl (NVOC), nitropiperonyl oxycarbonyl (NPOC), α-methyl-nitroveratryloxycarbonyl (MeNVOC), α-methyl-nitropiperonyloxycarbonyl (MeNPOC), 1-pyrenylmethyloxycarbonyl (PYMOC), and the benzylic forms of each of these (i.e., NNP, MBPM, NV, NP, MeNV, MeNP and PYM, respectively), with MeNPOC, NPPOC and MBPMOC being most preferred.

Protection strategies may be optimized for different phosphoramidite nucleosides to enhance synthesis efficiency. Examples of such optimized synthesis methods are reported in, e.g., U.S. patent application Ser. No. 08/445,332 filed May 19, 1995, incorporated herein by reference in its entirety for all purposes. Generally, these optimization methods involve selection of particular protecting groups for protection of the $O^6$ group of guanosine, which can markedly improve coupling efficiencies in the synthesis of guanosine containing oligonucleotides. Similarly, selection of the appropriate protecting group for protection of the $N^2$ group of guanosine can also result in such an improvement in the absence of protection of the $O^6$ group. For example, suitable protecting groups for protection of the $N^2$ group, where the $O^6$ group is also protected, include, e.g., mono- or diacyl protecting groups, triarylmethyl protecting groups, e.g., DMT and MMT, and amidine type protecting groups, e.g., N,N-dialkylformamidines. Particularly preferred protecting groups for the $N^2$ group include, e.g., DMT, DMF, PAC, Bz and Ibu.

Protection of the $O^6$ group will generally be carried out using carbamate protecting groups such as —C(O)NX$_2$, where X is alkyl, or aryl; or the protecting group —CH$_2$CH$_2$Y, where Y is an electron withdrawing group such as cyano, p-nitrophenyl, or alkyl- or aryl-sulfonyl; and aryl protecting groups. In a particularly preferred embodiment, the $O^6$ group is protected using a diphenylcarbamoyl protecting group (DPC).

Alternatively, improved coupling efficiencies may be achieved by selection of an appropriate protecting group for only the $N^2$ group. For example, where the $N^2$-PAC protecting group is substituted with an Ibu protecting group, a substantial improvement in coupling efficiency is seen, even without protection of the $O^6$ group.

A variety of modifications can be made to the above-described synthesis methods. For example, in some embodiments, it may be desirable to directly transfer or add photolabile protecting groups to functional groups, e.g., NH$_2$, OH, SH or the like, on a solid support. For these methods, conventional peptide or oligonucleotide monomers or building blocks having chemically removable protecting groups are used instead of monomers having photoprotected functional groups. In each cycle of the synthesis procedure, the monomer is coupled to reactive sites on the substrate, e.g., sites deprotected in a prior photolysis step. The protecting group is then removed using conventional chemical techniques and replaced with a photolabile protecting group prior to the next photolysis step.

A number of reagents will effect this replacement reaction. Generally, these reagents will have the following generic structure:

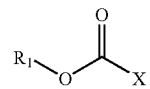

where $R_1$ is a photocleavable protecting group and X is a leaving group, i.e., from the parent acid HX. The stronger acids typically correspond to better leaving groups and thus, more reactive acylating agents.

Examples of suitable reagents are described in U.S. Patent Appl. Pub. No. 20040105932, incorporated herein by reference in its entirety for all purposes.

Conditions for carrying out this transfer are similar to those used for coupling reaction in solid phase peptide synthesis, or for the capping reaction in solid phase oligonucleotide synthesis. The solid phase amine, hydroxyl or thiol groups are exposed to a solution of the protecting group coupled to the leaving group, e.g., MeNPOC-X in a non-nucleophilic organic solvent, e.g., DMF, NMP, DCM, THF, ACN, and the like, in the presence of a base catalysts, such as pyridine, 2,6-lutidine, TEA, DIEA and the like. In cases where acylation of surface groups is less efficient under these conditions, nucleophilic catalysts such as DMAP, NMI, HOBT, HOAT and the like, may also be included to accelerate the reaction through the in situ generation of more reactive acylating agents. This would typically be the case where a derivative is preferred for its longer term stability in solution, but is not sufficiently reactive without the addition of one or more of the catalysts mentioned above. On automated synthesizers, it is generally preferable to choose a reagent which can be stored for longer terms as a stable solution and then activated with the catalysts only when needed, i.e., in the reactor system flow cell, or just prior to the addition of the reagent to the flow cell.

In addition to the protection of amine groups and hydroxyl groups in peptide and oligonucleotide synthesis, the reagents and methods described herein may be used to transfer photolabile protecting groups directly to any nucleophilic group, either tethered to a solid support or in solution.

E. Individual Processing
Flow Cell/Reactor System

In one embodiment, the substrate preparation process of the present invention is performed in a single unit operation. In this embodiment, the substrate wafer is mounted in a flow cell during, for example, both the photolysis and chemistry or monomer addition steps. In particular, the substrate is mounted in a reactor system that allows for the photolytic exposure of the synthesis surface of the substrate to activate the functional groups thereon. Solutions containing chemical monomers are then introduced into the reactor system and contacted with the synthesis surface, where the monomers can bind with the active functional groups on the substrate surface. The monomer containing solution is then removed from the reactor system, and another photolysis step is performed, exposing and activating different selected regions of the substrate surface. This process is repeated until the desired polymer arrays are created.

Reactor systems and flow cells that are particularly suited for the combined photolysis/chemistry process include those described in, e.g., U.S. Pat. No. 5,424,186 and U.S. Patent Appl. Pub. 20040105932, each of which is incorporated herein by reference in its entirety for all purposes.

Photolysis

As described above, photolithographic methods can be used to activate selected regions on the surface of the substrate. Specifically, functional groups on the surface of the substrate or present on growing polymers on the surface of the substrate, are protected with photolabile protecting groups. Activation of selected regions of the substrate is carried out by exposing selected regions of the substrate surface to activation radiation, e.g., light within the effective wavelength range, as described previously. Selective exposure is typically carried out by shining a light source through a photolithographic mask. Alternate methods of exposing selected regions may also be used, e.g., fiber optic faceplates and the like.

Because the individual feature sizes on the surface of the substrate prepared according to the processes described herein can typically range as low as 1-10 μm, the effects of reflected or refracted light at the surface of the substrate can have significant effects upon the ability to expose and activate features of this size. One method of reducing the occurrence of reflected light is to incorporate a light absorptive material as the back surface of the flow cell, as described above. Refraction of the light as it enters the flow cell can also result in a loss in feature resolution at the synthesis surface of the substrate resulting from refraction and reflection. To alleviate this problem, during the photolysis step, it is generally desirable to fill the flow cell with an index matching fluid ("IMF") to match the refractive index of the substrate, thereby reducing refraction of the incident light and the associated losses in feature resolution. The index matching fluid will typically have a refractive index that is close to that of the substrate. Typically, the refractive index of the IMF will be within about 10% that of the substrate, and preferably within about 5% of the refractive index of the substrate. Refraction of the light entering the flow cell, as it contacts the interface between the substrate and the IMF is thereby reduced. Where synthesis is being carried out on, e.g., a silica substrate, a particularly preferred IMF is dioxane which has a refractive index roughly equivalent to the silica substrate.

The light source used for photolysis is selected to provide a wavelength of light that is photolytic to the particular protecting groups used, but which will not damage the forming polymer sequences. Typically, a light source which produces light in the UV range of the spectrum will be used. For example, in oligonucleotide synthesis, the light source typically provides light having a wavelength above 340 nm to effect photolysis of the photolabile protecting groups without damaging the forming oligonucleotides. This light source is generally provided by a Hg-Arc lamp employing a 340 nm cut-off filter (i.e., passing light having a wavelength greater than 340-350 nm). Typical photolysis exposures are carried out at from about 6 to about 10 times the exposed half-life of the protecting group used, with from 8-10 times the half-life being preferred. For example, MeNPOC, a preferred photolabile protecting group, has an exposed half-life of approximately 6 seconds, which translates to an exposure time of approximately 36 to 60 seconds.

Photolithographic masks used during the photolysis step typically include transparent regions and opaque regions, for exposing only selected portions of the substrate during a given photolysis step. Typically, the masks are fabricated from glass that has been coated with a light-reflective or absorptive material, e.g., a chrome layer. The light-reflective or absorptive layer is etched to provide the transparent regions of the mask. These transparent regions correspond to the regions to be exposed on the surface of the substrate when light is shown through the mask.

In general, it is desirable to produce arrays with smaller feature sizes, allowing the incorporation of larger amounts of information in a smaller substrate area, allowing interrogation of larger samples, more definitive results from an interrogation and greater possibility of miniaturization. Alternatively, by reducing feature size, one can obtain a larger number of arrays, each having a given number of features, from a single substrate wafer. The result is substantially higher product yields for a given process. This technique, generally referred to as "die shrinking" is commonly used in the semiconductor industry to enhance product outputs or to reduce chip sizes following a over-sized test run of a manufacturing process.

In seeking to reduce feature size, it is important to maximize the contrast between the regions of the substrate exposed to light during a given photolysis step, and those regions which remain dark or are not exposed. By "contrast" is meant the sharpness of the line separating an exposed region and an unexposed region. For example, the gradient of activated to non-activated groups running from an activated or exposed region to a non-exposed region is a measure of the contrast. Where the gradient is steep, the contrast is high, while a gradual gradient indicates low or poor contrast. One cause of reduced contrast is "bleed-over" from exposed regions to non-exposed regions during a particular photolysis step. In certain embodiments, contrast between features is enhanced through the front side exposure of the substrate. Front side exposure reduces effects of diffraction or divergence by allowing the mask to be placed closer to the synthesis surface. Additionally, and perhaps more importantly, refractive effects from the light passing through the substrate surface prior to exposure of the synthesis surface are also reduced or eliminated by front side exposure.

Contrast between features may also be enhanced using a number of other methods. For example, the level of contrast degradation between two regions generally increases as a function of the number of differential exposures or photolysis steps between the two regions, i.e., incidences where one region is exposed while the other is not. The greater the number of these incidences, the greater the opportunity for bleed-over from one region to the other during each step and the lower the level of contrast between the two regions. Translated into sequence information, it follows that greater numbers of differences between polymers synthesized in adjacent regions on a substrate can result in reduced contrast between the regions. Namely, the greater the number of differences in two polymer sequences, the greater the number of incidences of a region bearing the first polymer being exposed while the other was not. These effects are termed "edge" effects as they generally occur at the outer edges of the feature.

It is thus desirable to minimize these edge effects to enhance contrast in synthesis. Accordingly, in one aspect, the present invention provides a method of enhancing contrast by reducing the number of differential synthesis/photolysis steps between adjacent polymer sequence containing regions throughout an array.

One method of edge minimization is to divide the polymers to be sequenced into blocks of related polymers, leaving blank lanes between the blocks to prevent bleed-over into other blocks. While this method is effective in reducing edge effects, it requires the creation of a specific algorithm for each new tiling strategy. That is, the layout of each block in terms of probe location will depend upon the tiled sequence. In one aspect, the present invention provides methods for aligning polymer synthesis steps on an array whereby the number of differential synthesis steps is reduced, and/or the syntheses in adjacent regions of the array are optimized for similarity. An example of a typical photolysis synthesis strategy is set forth in U.S. Patent Appl. Pub. No. 20040105932, incorporated herein by reference in its entirety for all purposes.

Photo Acid Generator and Acid Scavenger

One embodiment of the present invention includes a photochemical amplification method wherein photon radiation signals are converted into chemical signals in a manner that increases the effective quantum yield of the photon in the desired reaction. The use of photochemical amplification in methods of synthesizing patterned arrays (PASPA) is particularly advantageous since the time and the intensity of irradiation required to remove protective groups is decreased relative to known direct photochemical methods. Additionally, photoacid generators (PAG) generate acid directly upon radiation to remove protecting groups.

In general, radiation signals are detected by a catalyst system including, for example, a photo activated catalyst (PAC). The catalyst activates an enhancer, which increases the effective quantum yield of the photons in subsequent chemical reactions. Such subsequent reactions include the removal of protective groups in the synthesis of patterned arrays. It is desirable to remove all the protecting groups in a very precise location without removing protecting groups outside of the desired location. To prevent removal of protective groups in undesirable locations, a catalyst scavenger in some cases may be added but is not necessary to compete for the catalyst, thus enabling the user to more specifically define the area effected by the radiation signals.

In certain embodiments, a photo activated acid catalyst (PAAC) is irradiated. The resulting acid produced from the PAAC activates an enhancer to undergo an acid-catalyzed reaction to itself produce an acid that removes acid labile protecting groups from a linker molecule or synthesis intermediate. The combination of PACs and enhancers converts and amplifies the photon signal irradiated on the surface of the substrate. Because of the amplification, the effective quantum yield of the radiation directed at the surface of the substrate is much larger than one, resulting in high sensitivity.

One way of controlling acid catalyst "bleed-over" is the addition of an acid scavenger which serves to soak up the acid catalyst in competition with the photo activation reaction. Adjusting the concentration of acid catalyst aids in fine tuning the area in which the protecting groups are removed.

According to one embodiment of the present invention, linker molecules having reactive functional groups protected by protecting groups are provided on the surface of a substrate. A catalyst system including a PAC and an enhancer are also provided on the surface. In some embodiments, an acid catalyst scavenger may also be added. A set of selected regions on the surface of the substrate is exposed to radiation using well-known lithographic methods as discussed herein (See Thompson et al. (1994) *American Chemical Society*, 1994:212, incorporated herein by reference in its entirety for all purposes).

The PAC catalyst activated by the region-selective irradiation discussed above acts to initiate a reaction of the enhancer. The enhancer produces at least one product that removes the protecting groups from the linker molecules in the first selected regions. Preferably, the enhancer is capable of removing protective groups in a catalytic manner. In some cases an acid scavenger may be added to react with the acid catalyst, limiting the amount of acid catalyst available to react with the enhancer. The substrate is then washed or otherwise contacted with a first monomer that reacts with exposed functional groups on the linker molecules. Those bound monomers are termed first-bound monomers.

A second set of selected regions is, thereafter, exposed to radiation. The radiation-initiated reactions remove the protecting groups on molecules in the second set of selected regions, i.e., the linker molecules and the first-bound monomers. The substrate is then contacted with a second monomer containing a removable protective group for reaction with exposed functional groups. This process is repeated to selectively apply monomers until polymers of a desired length and desired chemical sequence are obtained. Protective groups are then optionally removed and the sequence is, thereafter, optionally capped. Side chain protective groups, if present, are also optionally removed.

In one preferred embodiment, the monomer is a 2'-deoxynucleoside phosphoramidite containing an acid removable protecting group at its 5' hydroxyl group. In an alternate embodiment, the protecting group is present at the 3' hydroxyl group if synthesis of the polynucleotide is from the 5' to 3' direction. The nucleoside phosphoramidite is represented by the following formula:

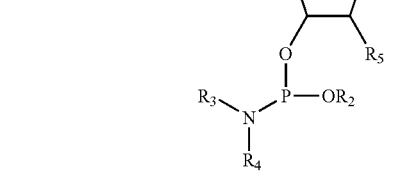

wherein the base is adenine, guanine, thymine, cytosine or any other nucleobase analog; $R_1$ is a protecting group which makes the 5' hydroxyl group unavailable for reaction and includes dimethoxytrityl, MeNPOC, tert-butyloxycarbonyl or any of the protecting groups previously identified; $R_2$ is cyanoethyl, methyl, t-butyl, trimethylsilyl and the like; $R_3$ and R4 are isopropyl, cyclohexone and the like; and $R_5$ is hydrogen, NR'R", OR, SR, CRR'R", or OSi(R''')$_3$ wherein R, R', R", and R''' are hydrogen, alkyl and the like. Exocyclic amines present on the bases can also be protected with acyl protecting groups such as benzoyl, isobutyryl, phenoxyacetyl and the like. The linker molecule contains an acid- or base-removable protecting group. Useful linker molecules are well known to those skilled in the art and representative examples include oligo ethers such as hexaethylene glycol, oligomers of nucleotides, esters, carbonates, amides and the like. Useful protecting groups include those previously listed and others known to those skilled in the art.

In another preferred embodiment, the monomer is an amino acid containing an acid- or base-removable protecting group at its amino or carboxy terminus and the linker molecule terminates in an amino or carboxy acid group bearing an acid- or base removable protecting group. Protecting groups include tert-butyloxycarbonyl, 9-fluorenylmethyloxycarbonyl, and any of the protective groups previously mentioned and others known to those skilled in the art.

In a preferred embodiment the catalyst scavenger may be an acid scavenger such as an amine and more specifically may be trioctylamine or 2,5-di-tertbutylanaline. Other acid scavengers include carboxylate salts and hydroxides. See, e.g. Huang (1999) *Proc. SPIE-Int. Soc. Opt. Eng.* 3678:1040, incorporated herein by reference in its entirety for all purposes. Those of skill in the art will be familiar with other acid scavengers which will be appropriate for the present invention.

In another preferred embodiment, the catalyst scavenger may be a base scavenger such as acetic acid or trichloro acetic acid, Other base scavengers include phosphoric acid, sulfuric acid or any other carboxylic acid. Care should be taken to chose a base scavenger which will not interfere with or destroy the monomer. Those of skill in the art will be familiar with other base scavengers which will be appropriate for the present invention.

It is apparent to those skilled in the art that photochemically amplified radiation-based activation is not limited to photo activated enhancers or catalysts or to acid or base production cascades. Various compounds or groups can produce catalysts or enhancers in response to radiation exposure. Non-limiting examples include photogeneration of radicals using diphenylsulfide, benzoylperoxide, 2,2'-azobis(butyronitrile), benzoin and the like; cations such as triarylsulfonium salts, diaryl iodonium salts and the like; and anions. Furthermore, it is apparent to those of skill in the art that the catalyst scavengers are not limited to acid or base scavengers but may include any other compound which will interfere with the catalysts' ability to interact with the enhancer.

In a preferred embodiment, the catalyst and catalyst scavenger are capable of engaging in a cyclic reaction. For example, a compound X comprises subcompound Y which is capable of acting as a catalyst and subcompound Z which is capable of acting as a catalyst scavenger. Compound X is capable of entering into an excited state after exposure to radiation. During this excited state the subcompounds Y and Z separate and subcompound Y is free to catalyze removal of protecting groups. In a further preferred embodiment, the subcompounds Y and Z are capable of remaining in this excited state for only a very short period of time. This time period may be from between a few nanoseconds to a few milliseconds. After the time period lapses, subcompounds Y and Z are free to interact with one another once again forming compound X Exposure to radiation may then initiate another cycle. In a preferred embodiment, compound X is very stable prior to exposure to radiation, and only capable of interacting with other molecules during the excited state.

The selection of radiation sources is based upon the sensitivity spectrum of the compound to be irradiated. Potential damage to synthesis substrates, intermediates, or products is also considered. In some preferred embodiments, the radiation could be ultraviolet (UV), infrared (IR), or visible light. In a specific embodiment, the radiation source is a light beam with a wavelength in the range of from 190-500 nm, preferably from 250-450 nm, more preferably from 365-400 nm. Specific radiation wavelengths include 193 nm, 254 mn, 313 mm, 340 nm, 396 nm, 413 nm, 436 run, and 500 nm. Suitable light sources include high pressure mercury arc lamps and are readily commercially available from Oriel, OAI, Cannon, A-B Manufacturing and the like. In embodiments utilizing the catalytic system, the sensitivity spectrum of the RAC can be altered by providing radiation sensitizers. The energy of the sensitizer must be matched to the PA(C and include 2-ethyl-9,10-dimethoxy-anthracene, perylene, phenothiazine, xanthone and the like. Many radiation sensitizers are known to those skilled in the art and include those previously mentioned. It is to be understood that one of ordinary skill in the art will be able to readily identify additional radiation sensitizers based upon the present disclosure.

In addition to the foregoing, aspects of the invention include additional methods which can be used to generate an array of oligonucleotides on a single substrate are described in U.S. Pat. Nos. 5,677,195 and 5,384,261, and in PCT Publication No. WO 93/09668, each of which is incorporated herein by reference in its entirety for all purposes. In the methods disclosed in these applications, reagents are delivered to the substrate by either (1) flowing within a channel defined on predefined regions or (2) "spotting" on predefined regions or (3) through the use of photoresist. However, other approaches, as well as combinations of spotting and flowing, may be employed. In each instance, certain activated regions of the substrate are mechanically separated from other regions when the monomer solutions are delivered to the various reaction sites.

In one aspect, a typical "flow channel" method is applied to the compounds and libraries of the present invention, and can generally be described as follows. Diverse polymer sequences are synthesized at selected regions of a substrate or solid support by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer A flows through or is placed in all or some of the channel(s). The channels provide fluid contact to the first selected regions, thereby binding the monomer A on the substrate directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate.

After the substrate is activated, monomer A can be flowed through some of the channels, monomer B can be flowed through other channels, a monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

In another aspect, the "spotting" methods of preparing compounds and libraries of the present invention can be implemented in much the same manner as the flow channel methods. For example, a monomer A can be delivered to and coupled with a first group of reaction regions which have been appropriately activated. Thereafter, a monomer B can be delivered to and reacted with a second group of activated reaction regions. Unlike the flow channel embodiments described above, reactants are delivered by directly depositing (rather than flowing) relatively small quantities of them in selected regions. In some steps, of course, the entire substrate surface can be sprayed or otherwise coated with a solution. In preferred embodiments, a dispenser moves from region to region, depositing only as much monomer as necessary at each stop. Typical dispensers include a micropipette to deliver the monomer solution to the substrate and a robotic system to control the position of the micropipette with respect to the substrate. In other embodiments, the dispenser includes a series of tubes, a manifold, an array of pipettes, or the like so that various reagents can be delivered to the reaction regions simultaneously.

F. Assembly of Probe Array Cartridges

Following synthesis, final deprotection and other finishing steps, eg. polymer coat removal where necessary, the substrate wafer can be assembled for use as individual substrate segments. Assembly typically employs the steps of separating the substrate wafer into individual substrate segments, and inserting or attaching these individual segments to a housing which includes a reaction chamber in fluid communication with the front surface of the substrate segment, e.g., the surface having the polymers synthesized thereon.

Methods of separating and packaging substrate wafers are described in substantial detail in Published PCT Application No. 95/33846, which is hereby incorporated herein by reference in its entirety for all purposes.

Typically, the arrays are synthesized on the substrate wafer in a grid pattern, with each array being separated from each other array by a blank region where no compounds have been synthesized. These separating regions are termed "streets." The wafer typically includes a number of alignment marks located in these streets. These marks serve a number of purposes, including aligning the masks during synthesis of the arrays as described above, separation of the wafer into individual chips and placement of each chip into its respective housing for subsequent use, which are both described in greater detail below.

Generally, the substrate wafer can be separated into a number of individual substrates using scribe and break methods that are well known in the semiconductor manufacturing industry. For example, well known scribe and break devices may be used for carrying out the separation steps, e.g., a fully programmable computer controlled scribe and break devices, such as a DX-III Scriber-Breaker manufactured by Dynatex International (Santa Rosa, Calif.), or the LCD-1 scriber/dicer manufactured by Loomis Industries Inc. (St. Helena, Calif.). The steps typically involve scribing along the desired separation points, e.g., between the individual synthesized arrays on the substrate wafer surface, followed by application of a breaking force along the scribe line. For example, typical scribe and break devices break the wafer by striking the bottom surface of the wafer along the scribe lines with an impulse bar, or utilizing a three point beam substrate bending operation. The shock from the impulse bar fractures the wafer along the scribe line. Because the majority of force applied by the impulse bar is dissipated along the scribe line, the device is able to provide high breaking forces without exerting significant force on the substrate itself, allowing separation of the wafer without damaging the individual chips.

In alternative methods, the wafer may be separated into individual segments by, e.g., sawing methods, such as those described in U.S. Pat. No. 4,016,855, incorporated herein by reference in its entirety for all purposes.

Once the wafer is separated into individual segments, these segments may be assembled in a housing that is suited for the particular analysis for which the array will be used. Examples of methods and devices for assembling the substrate segments or arrays in cartridges are described in, e.g., U.S. Pat. No. 5,945,334, incorporated herein by reference in its entirety for all purposes. Typically, the housing includes a body having a cavity disposed within it. The substrate segment is mounted over the cavity on the body such that the front side of the segment, e.g., the side upon which the polymers have been synthesized, is in fluid communication with the cavity. The bottom of the cavity may optionally include a light absorptive material, such as a glass filter or carbon dye, to prevent impinging light from being scattered or reflected during imaging by detection systems. This feature improves the signal-to-noise ratio of such systems by significantly reducing the potential imaging of undesired reflected light.

The cartridge also typically includes fluid inlets and fluid outlets for flowing fluids into and through the cavity. A septum, plug, or other seal may be employed across the inlets and/or outlets to seal the fluids in the cavity. The cartridge also typically includes alignment structures, e.g., alignment pins, bores, and/or an asymmetrical shape to ensure correct insertion and/or alignment of the cartridge in the assembly devices, hybridization stations, and reader devices. Example of certain embodiments of cartridges are described in U.S. Patent Appl. Pub. No. 20040105932, incorporated herein by reference in its entirety for all purposes.

In a preferred embodiment, the bottom casing with selected cavity dimensions may be removed from the middle and top casings and replaced with another bottom casing with different cavity dimensions. This allows a user to attach a chip having a different size or shape by changing the bottom casing, thereby providing ease in using different chip sizes, shapes, and the like. Of course, the size, shape, and orientation of the cavity will depend upon the particular application. The body of the cartridge may generally be fabricated from one or more parts made using a number of manufacturing techniques. In preferred aspects, the cartridge is fabricated from two or more injection molded plastic parts. Injection molding enables the casings to be formed inexpensively. Also, assembling the cartridge from two parts simplifies the construction of various features, such as the internal channels for introducing fluids into the cavity. As a result, the cartridges may be manufactured at a relatively low cost.

The substrate segment may be attached to the body of the cartridge using a variety of methods. In preferred aspects, the substrate is attached using an adhesive. Preferred adhesives are resistant to degradation under conditions to which the cartridge will be subjected. In particularly preferred aspects, an ultraviolet cured adhesive attaches the substrate segment to the cartridge. Devices and methods for attaching the substrate segment are described in Published PCT Application No. 95/33846, incorporated herein by reference in its entirety for all purposes. Particularly preferred adhesives are commercially available from a variety of commercial sources, including Loctite Corp. (Irvine, Calif.) and Dymax Corp. (Torrington, Conn.).

A variety of modifications can be incorporated in the assembly methods and devices that are generally described herein, and these too are outlined in greater detail in published PCT Application No. 95/33846, incorporated herein by reference in its entirety for all purposes.

Upon completion, the cartridged substrate will have a variety of uses. For example, the cartridge can be used in a variety of sequencing by hybridization ("SBH") methods, sequence checking methods, diagnostic methods and the like. Arrays which are particularly suited for sequence checking and SBH methods are described in, e.g., U.S. patent application Ser. No. 08/505,919, filed Jul. 24, 1995, Ser. No. 08/441,887, filed May 16, 1995, Ser. No. 07/972,0075 filed Nov. 5, 1992, each of which is incorporated herein by reference in its entirety for all purposes.

Typically, in carrying out these methods, the cartridged substrate is mounted on a hybridization station where it is connected to a fluid delivery system. The fluid delivery system is connected to the cartridge by inserting needles into the inlet and outlet ports through the septa disposed therein. In this manner, various fluids are introduced into the cavity for contacting the probes synthesized on the front side of the substrate segment, during the hybridization process.

Usually, hybridization is performed by first exposing the sample with a pre-hybridization solution. Next, the sample is incubated under binding conditions for a suitable binding period with a sample solution that is to be analyzed. The sample solution generally contains a target molecule, e.g., a target nucleic acid, the presence or sequence of which is of interest to the investigator. Binding conditions will vary depending on the application and are selected in accordance with the general binding methods known including those referred to in: Maniatis et al., *Molecular Cloning: A Laboratory Manual* (1989), 2nd Ed., Cold Spring Harbor, N.Y.; Berger and Kimmel, *Methods in Enzymology*, Volume 152, Guide to Molecular Cloning Techniques (1987), Academic Press, Inc., San Diego, Calif.; *Laboratory Techniques in Biochemistry and Molecular Biology*, Vol. 24: Hybridization With Nucleic Acid Probes, P. Tijssen, ed. Elsevier, N.Y., (1993); and Young and Davis (1983) *Proc. Natl. Acad. Sci. USA* 80:1194, each of which is incorporated herein by reference in its entirety for all purposes. In certain embodiments, the solution may contain about 1 M salt and about 1 to 50 nM targets. Optionally, the fluid delivery system includes an agitator to improve mixing in the cavity, which shortens the incubation period. Finally, the sample is washed with a buffer, which may be 6×SSPE buffer, to remove the unbound targets. In some embodiments, the cavity is filled with the buffer after washing the sample.

Following hybridization and appropriate rinsing/washing, the cartridged substrate may be aligned on a detection or imaging system, such as those disclosed in U.S. Pat. Nos. 5,143,854 and 5,631,734, and U.S. patent application Ser. No. 08/465,782, filed Jun. 6, 1995, and Ser. No. 08/456,598, filed Jun. 1, 1995, each of which is incorporated herein by reference in its entirety for all purposes. Such detection systems may take advantage of the cartridge's asymmetry (i.e., non-flush edge) by employing a holder to match the shape of the cartridge specifically. Thus, the cartridge is assured of being properly oriented and aligned for scanning. The imaging systems are capable of qualitatively analyzing the reaction between the probes and targets. Based on this analysis, sequence information of the targets is extracted. In accordance with a preferred embodiment of the present invention, confocal fluorescence scanning is conducted front side, since the excitation light would otherwise be blocked by the substrate.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. A method of performing confocal laser microscopy on a polymer array disposed on a silicon wafer substrate, the method comprising the steps of:

providing a silicon wafer substrate having a top side and a bottom side;

coating the top side of the substrate with a transparent oxide layer to provide an oxide coated wafer;

depositing a reactive functional group comprising a labile protecting group substantially uniformly across the transparent oxide layer, wherein the labile protecting group is NNPOC or MBPMOC;

selectively removing one or more of the labile protecting groups from predefined regions of the wafer to provide exposed functional groups in the predefined regions;

reacting the exposed functional groups with a nucleic acid comprising a reactive functional group and a labile protecting group;

repeating the steps of selectively removing and reacting to produce the polymer array;

hybridizing the polymer array with a plurality of ligands; and assaying for one or more hybridized ligands using confocal laser fluorescence microscopy to detect hybridization.

2. The method of claim 1, wherein the oxide layer has a thickness of at least 3,500 angstroms.

3. The method of claim 1, wherein the oxide layer has a thickness of at least 35,000 angstroms.

4. The method of claim 1, wherein the labile protecting group is removed by activating a photoacid generator with light of an appropriate wavelength to produce acid.

5. The method of claim 4, wherein the photoacid generator is an ionic photoacid generator or a non-ionic photoacid generator.

6. The method of claim 4, wherein the photoacid generator is an ionic photoacid generator.

7. The method of claim 4, wherein the photoacid generator is a non-ionic photoacid generator.

8. The method of claim 7, wherein the non-ionic photoacid generator is 2,6-dinitrobenzyl tosylate.

9. The method of claim 6, wherein the ionic photoacid generator is an onium salt.

10. The method of claim 9, wherein the onium salt is bis-(4-t-butyl phenyl) iodonium $PF6^-$.

* * * * *